US011564662B2

(12) United States Patent
Sato

(10) Patent No.: US 11,564,662 B2
(45) Date of Patent: *Jan. 31, 2023

(54) ULTRASOUND DIAGNOSIS APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventor: Takeshi Sato, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 423 days.

This patent is subject to a terminal disclaimer.

(21) Appl. No.: 16/200,692

(22) Filed: Nov. 27, 2018

(65) Prior Publication Data

US 2019/0159763 A1 May 30, 2019

(30) Foreign Application Priority Data

Nov. 30, 2017 (JP) .............................. JP2017-230839

(51) Int. Cl.
*A61B 8/08* (2006.01)
*A61B 8/14* (2006.01)
(Continued)

(52) U.S. Cl.
CPC .............. *A61B 8/5276* (2013.01); *A61B 8/06* (2013.01); *A61B 8/0891* (2013.01); *A61B 8/14* (2013.01);
(Continued)

(58) Field of Classification Search
CPC ................. G01S 7/52–64; G01S 15/00; G01S 15/52–62; A61B 8/5276; A61B 8/06;
(Continued)

(56) References Cited

U.S. PATENT DOCUMENTS 4,324,258 A * 4/1982 Huebscher ............... A61B 8/06
600/455
7,786,909 B2 * 8/2010 Udupa .................. H03M 1/129
341/118

(Continued)

FOREIGN PATENT DOCUMENTS

JP 2010-259799 11/2010
JP 2014-009794 1/2014
(Continued)

*Primary Examiner* — Sean D Mattson
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to speculate saturation of reflected-wave signals observed before a phased addition process performed by using the reflected-wave signals, in accordance with an intensity of reflected-wave data generated through the phased addition process, the reflected-wave signals being generated by transmitting an ultrasound wave with respect to mutually the same scanning line, and the processing circuitry is configured to output a result of the speculation. The processing circuitry is configured to cause a display to display data based on the result of the speculation.

19 Claims, 15 Drawing Sheets

(51) Int. Cl.
*A61B 8/00* (2006.01)
*A61B 8/06* (2006.01)
(52) U.S. Cl.
CPC ............ *A61B 8/461* (2013.01); *A61B 8/5207* (2013.01); *A61B 8/5223* (2013.01); *A61B 8/5253* (2013.01)
(58) Field of Classification Search
CPC ....... A61B 8/0891; A61B 8/14; A61B 8/5253; A61B 8/5223; A61B 8/5207; A61B 8/461; G16H 50/30
See application file for complete search history.

(56) References Cited

U.S. PATENT DOCUMENTS

| | | | |
|---|---|---|---|
| 2008/0110263 A1* | 5/2008 | Klessel | G01S 7/52085 73/602 |
| 2010/0280384 A1 | 11/2010 | Song et al. | |
| 2011/0096958 A1* | 4/2011 | Fukumoto | A61B 8/08 382/106 |
| 2014/0039317 A1* | 2/2014 | Sato | A61B 8/5207 600/443 |
| 2015/0040552 A1 | 2/2015 | Hashimoto | |
| 2015/0282787 A1* | 10/2015 | Sato | A61B 8/488 600/441 |
| 2015/0320395 A1* | 11/2015 | Sato | A61B 8/06 600/455 |
| 2015/0366540 A1* | 12/2015 | Sato | A61B 8/461 600/453 |
| 2016/0157827 A1* | 6/2016 | Kristoffersen | A61B 8/4494 600/447 |
| 2017/0071569 A1 | 3/2017 | Sato | |
| 2017/0071575 A1 | 3/2017 | Sato | |

FOREIGN PATENT DOCUMENTS

| | | |
|---|---|---|
| JP | 2014-158698 | 9/2014 |
| JP | 2015-181125 | 10/2015 |
| JP | 2015-181126 | 10/2015 |
| JP | 2017-055845 | 3/2017 |
| JP | 2017-055846 | 3/2017 |

\* cited by examiner

ULTRASOUND DIAGNOSIS APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2017-230839, filed on Nov. 30, 2017; the entire contents of which are incorporated herein by reference.

FIELD

Embodiments described herein related generally to an ultrasound diagnosis apparatus, a medical image processing apparatus, and a medical image processing method.

BACKGROUND

In recent years, for use in Color Flow Mapping (CFM) methods, a technique has been developed with which it is possible to display a small blood flow having low flowing velocity lower than the velocity of movements of the imaged patient, although such a display had conventionally been impossible as being hindered by tissues of the patient. For example, a blood flow imaging method employing an adaptive Moving Target Indicator (MTI) filter that uses an eigenvector has been disclosed. To implement this blood flow imaging method, a method has been disclosed by which a correlation matrix is calculated for an entire image so as to apply a single MTI filter matrix to the entire image, and another method has also been disclosed by which an image is separated into sections to calculate correlation matrices and to apply mutually-different MTI filter matrices to blocks.

When such a blood flow imaging method employing the adaptive MTI filter is implemented, a significant side lobe may be exhibited when signals are saturated. In particular, when a plane wave transmission or a diffuse wave transmission is performed, a problem arises where an arc-shaped artifact may occur. To cope with this problem, a method has been disclosed by which, for example, saturation is detected with respect to signals observed before a beam forming process.

DETAILED DESCRIPTION

An ultrasound diagnosis apparatus according to an embodiment includes processing circuitry. The processing circuitry is configured to speculate saturation of reflected-wave signals observed before a phased addition process performed by using the reflected-wave signals, in accordance with an intensity of reflected-wave data generated through the phased addition process, the reflected-wave signals being generated by transmitting an ultrasound wave with respect to mutually the same scanning line, and the processing circuitry is configured to output a result of the speculation. The processing circuitry is configured to cause a display to display data based on the result of the speculation.

Exemplary embodiments of an ultrasound diagnosis apparatus, a medical image processing apparatus, and a medical image processing method will be explained, with reference to the accompanying drawings. Possible embodiments are not limited to the embodiments described below. Further, the description of each of the embodiments is, in principle, similarly applicable to any other embodiment.

First Embodiment

Figure 1:
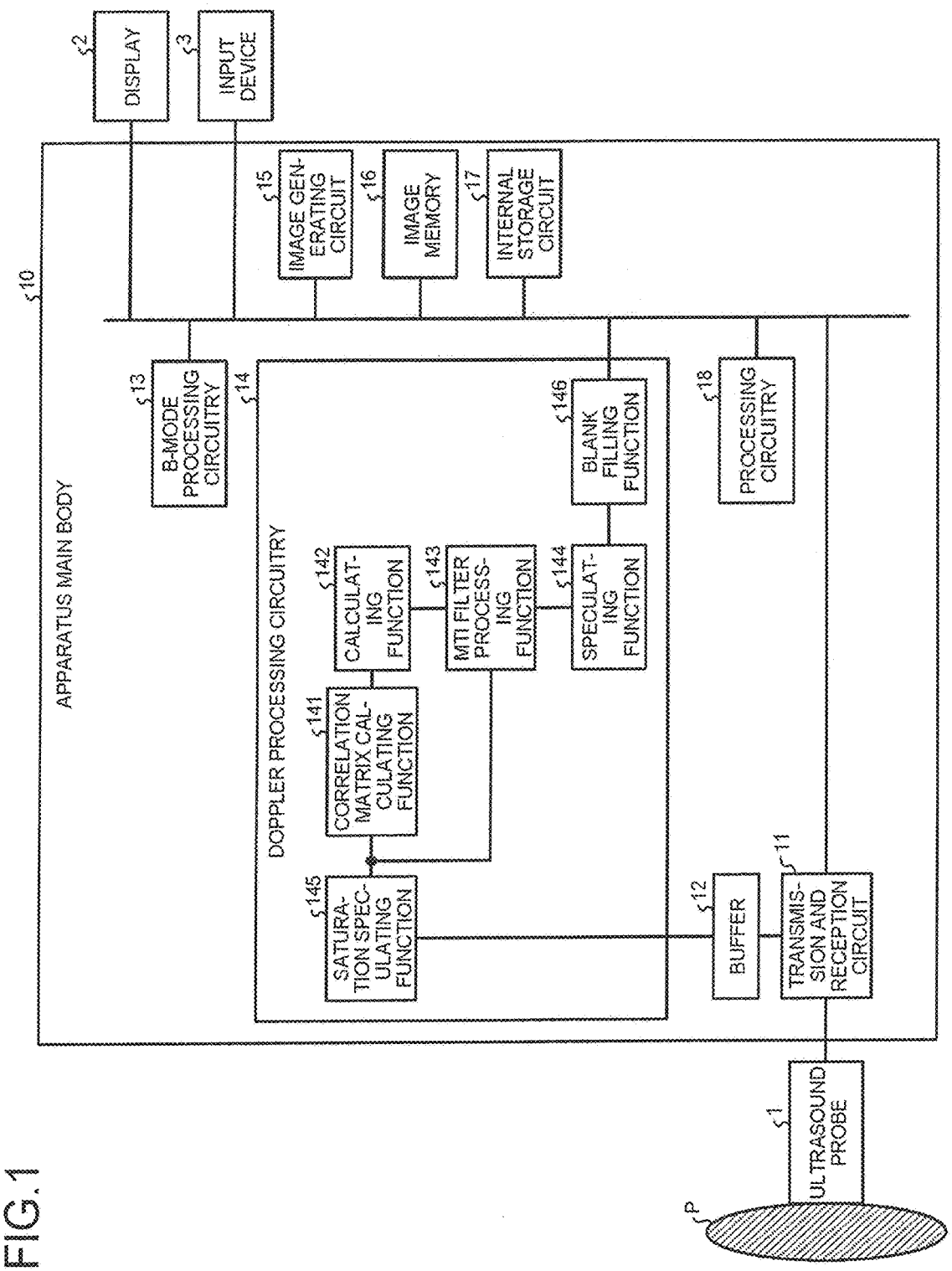
FIG. 1 is a block diagram illustrating an exemplary configuration of an ultrasound diagnosis apparatus according to a first embodiment.

First, a configuration of an ultrasound diagnosis apparatus according to a first embodiment will be explained. FIG. 1 is a block diagram illustrating an exemplary configuration of the ultrasound diagnosis apparatus according to the first embodiment. As illustrated in FIG. 1, the ultrasound diagnosis apparatus according to the first embodiment includes an ultrasound probe 1, a display 2, an input device 3, and an apparatus main body 10.

To transmit and receive ultrasound waves, the ultrasound probe 1 is connected to the apparatus main body 10. For example, the ultrasound probe 1 includes a plurality of piezoelectric transducer elements. Each of the plurality of piezoelectric transducer elements is configured to generate an ultrasound wave on the basis of a drive signal supplied thereto from a transmission and reception circuit 11 (explained later) included in the apparatus main body 10.

Further, each of the plurality of piezoelectric transducer elements included in the ultrasound probe 1 is configured to receive a reflected wave from an examined subject (hereinafter, "patient") P and to convert the received reflected wave into an electrical signal. Further, the ultrasound probe 1 includes matching layers provided for the piezoelectric transducer elements, as well as a backing member or the like that prevents the ultrasound waves from propagating rearward from the piezoelectric transducer elements. In this situation, the ultrasound probe 1 is detachably connected to the apparatus main body 10.

When an ultrasound wave is transmitted from the ultrasound probe 1 to the patient P, the transmitted ultrasound wave is repeatedly reflected on a surface of discontinuity of acoustic impedances at a tissue in the body of the patient P and is received as a reflected-wave signal by each of the plurality of piezoelectric transducer elements included in the ultrasound probe 1. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The first embodiment is applicable to both when the ultrasound probe 1 is a one-dimensional (1D) array probe configured to scan the patient P two-dimensionally and when the ultrasound probe 1 is a mechanical four-dimensional (4D) probe or a two-dimensional (2D) array probe configured to scan the patient P three-dimensionally.

The input device 3 includes a mouse, a keyboard, a button, a panel switch, a touch command screen, a foot switch, a trackball, a joystick, and/or the like. The input device 3 is configured to receive various types of setting requests from an operator of the ultrasound diagnosis apparatus and to transfer the received various types of setting requests to the apparatus main body 10.

The display 2 is configured to display a Graphical User Interface (GUI) used by the operator of the ultrasound diagnosis apparatus to input the various types of setting requests through the input device 3 and to display ultrasound image data or the like generated by the apparatus main body 10.

The apparatus main body 10 is an apparatus configured to generate the ultrasound image data on the basis of the reflected-wave signals received by the ultrasound probe 1. The apparatus main body 10 illustrated in FIG. 1 is an apparatus capable of generating two-dimensional ultrasound image data on the basis of two-dimensional reflected-wave signals and also capable of generating three-dimensional ultrasound image data on the basis of three-dimensional reflected-wave signals. It should be noted, however, that the first embodiment is also applicable when the apparatus main body 10 is an apparatus exclusively for two-dimensional data.

As illustrated in FIG. 1, the apparatus main body 10 includes the transmission and reception circuit 11, a buffer 12, B-mode processing circuitry 13, Doppler processing circuitry 14, an image generating circuit 15, an image memory 16, an internal storage circuit 17, and processing circuitry 18.

On the basis of an instruction from the processing circuitry 18 (explained later), the transmission and reception circuit 11 is configured to control transmission and reception of ultrasound waves performed by the ultrasound probe 1. The transmission and reception circuit 11 includes a pulse generator, a transmission delay circuit, a pulser, and the like and is configured to supply the drive signal to the ultrasound probe 1. The pulse generator is configured to repeatedly generate a rate pulse used for forming a transmission ultrasound wave, at a predetermined Pulse Repetition Frequency (PRF). Further, the transmission delay circuit is configured to apply a delay period that is required to converge the ultrasound wave generated from the ultrasound probe 1 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 1 with timing based on the rate pulses. In other words, by varying the delay periods applied to the rate pulses, the transmission delay circuit is able to arbitrarily adjust the transmission directions of the ultrasound waves transmitted from the surfaces of the piezoelectric transducer elements.

In this situation, the transmission and reception circuit 11 has a function that is able to instantly change the transmission frequency, the transmission drive voltage, and the like, for the purpose of executing a predetermined scan sequence on the basis of an instruction from the processing circuitry 18 (explained later). In particular, the function to change the transmission drive voltage is realized by using a linear-amplifier-type transmission circuit of which the value can be instantly switched or by using a mechanism configured to electrically switch between a plurality of power source units.

For example, under the control of the processing circuitry 18, the transmission and reception circuit 11 is configured to cause the ultrasound probe 1 to perform an ultrasound scan that uses an intra-frame data sequence as a Doppler data sequence (see Japanese Patent No. 3,724,846 and Japanese Patent Application Laid-open No. 2014-42823). For example, under the control of the processing circuitry 18, the transmission and reception circuit 11 causes the ultrasound probe 1 to perform a first ultrasound scan by which information about movements of moving members in a first scan range is obtained and further causes the ultrasound probe 1 to perform, in a time-division manner during the first ultrasound scan, an ultrasound scan in each of a plurality of sectional ranges into which a second scan range is separated, as a second ultrasound scan by which information about shapes of tissues in the second scan range is obtained.

Further, the transmission and reception circuit 11 includes an amplifying circuit, an Analog/Digital (A/D) converter, a reception delay circuit, an adder, a quadrature detecting circuit, and the like and is configured to generate reflected-wave data by performing various types of processes on the reflected-wave signals received by the ultrasound probe 1. The amplifying circuit is configured to amplify the reflected-wave signal for each of the channels and to perform a gain correcting process. The A/D converter is configured to perform an A/D conversion on the gain-corrected reflected-wave signals. The reception delay circuit is configured to apply a reception delay period required to determine reception directionality, to the digital data. The adder is configured to perform an adding process on the reflected-wave signals to which the reception delay period has been applied by the reception delay circuit. As a result of the adding process performed by the adder, reflected components from the direction corresponding to the reception directionality of the reflected-wave signals are emphasized. In this situation, the process of performing the adding process after adjusting phases by delaying the reception for each of the reflected-wave signals corresponding to the elements may be referred to as a phased addition process or a beam forming process.

Further, the quadrature detecting circuit is configured to convert the output signal from the adder into an In-phase signal (an I signal) and a Quadrature-phase signal (a Q signal) that are in a baseband. Further, the quadrature detecting circuit is configured to store the I signal and the Q signal (hereinafter, "IQ signals") into the buffer 12 as the reflected-wave data. Alternatively, the quadrature detecting circuit may store the output signal from the adder into the buffer 12 after converting the output signal into an analytic signal. The IQ signals or the analytic signal serves as a signal (a reception signal) containing phase information. In the following sections, the reflected-wave data output by the transmission and reception circuit 11 may be referred to as a reception signal.

When the patient P is to be two-dimensionally scanned, the transmission and reception circuit 11 is configured to cause a two-dimensional ultrasound beam to be transmitted from the ultrasound probe 1. Further, the transmission and reception circuit 11 is configured to generate two-dimensional reflected-wave data from the two-dimensional reflected-wave signals received by the ultrasound probe 1. In contrast, when the patient P is to be three-dimensionally scanned, the transmission and reception circuit 11 is configured to cause a three-dimensional ultrasound beam to be transmitted from the ultrasound probe 1. Further, the transmission and reception circuit 11 is configured to generate three-dimensional reflected-wave data from the three-dimensional reflected-wave signals received by the ultrasound probe 1.

The buffer 12 is a buffer configured to temporarily store therein the reflected-wave data (the I/Q signals) generated by the transmission and reception circuit 11. More specifically, the buffer 12 is configured to store therein the I/Q signals corresponding to a number of frames or the I/Q signals corresponding to a number of volumes. For example, the buffer 12 may be a First-In/First-Out (FIFO) memory and configured to store therein the I/Q signals corresponding to a predetermined number of frames. Further, for example, when the I/Q signals corresponding to another frame is newly generated by the transmission and reception circuit 11, the buffer 12 is configured to discard the I/Q signals corresponding to the one frame that was generated earliest and to store therein the newly-generated I/Q signals corresponding to the one frame.

The B-mode processing circuitry 13 and the Doppler processing circuitry 14 are each a signal processing unit configured to perform various types of signal processing processes on the reflected-wave data generated from the reflected-wave signals by the transmission and reception circuit 11. The B-mode processing circuitry 13 is configured to generate data (B-mode data) in which the signal intensity corresponding to each of a plurality of sampling points is expressed by a degree of brightness, by performing a logarithmic amplification, an envelope detecting process, a logarithmic compression, and/or the like on the reflected-wave data (the I/Q signals) read from the buffer 12.

Also, by performing a filtering process, the B-mode processing circuitry 13 is capable of varying the frequency band to be rendered in images, by varying the detected frequency. By using this function of the B-mode processing circuitry 13, the ultrasound diagnosis apparatus according to the first embodiment is capable of executing a harmonic imaging process such as a Contrast Harmonic Imaging (CHI) process, a Tissue Harmonic Imaging (THI) process, or the like. In other words, from the reflected-wave data of the patient P into whom a contrast agent has been injected, the B-mode processing circuitry 13 is configured to separate reflected-wave data (harmonic data or subharmonic data) of a harmonic component reflected by a contrast agent (microbubbles or bubbles) and reflected-wave data (fundamental wave data) of a fundamental wave component reflected by tissues on the inside of the patient P. The B-mode processing circuitry 13 is capable of generating B-mode data used for generating contrast enhanced image data, from reflected-wave data (a reception signal) of the harmonic component.

Further, by using the filtering function of the B-mode processing circuitry 13 mentioned above, the ultrasound diagnosis apparatus according to the first embodiment is capable of executing the Tissue Harmonic Imaging (THI) process. In other words, from the reflected-wave data of the patient P, the B-mode processing circuitry 13 is capable of separating the harmonic data or the subharmonic data represented by reflected-wave data (a reception signal) of the harmonic component. Further, the B-mode processing circuitry 13 is capable of generating B-mode data used for generating tissue image data from which noise components are eliminated, from the reflected-wave data (the reception signal) of the harmonic component.

Further, when performing the harmonic imaging process such as CHI or THI, the B-mode processing circuitry 13 is capable of extracting the harmonic component by using a method different from the abovementioned method that employs the filtering process. During the harmonic imaging process, an imaging method may be implemented such as an Amplitude Modulation (AM) method; a Phase Modulation (PM) method; or an AMPM method in which the AM method and the PM method are combined together. According to the AM method, the PM method, and the AMPM method, ultrasound wave transmission sessions having mutually-different amplitude levels and/or mutually-different phases are performed multiple times on mutually the same scanning line. As a result, the transmission and reception circuit 11 generates and outputs a plurality of pieces of reflected-wave data (the reception signals) for each of the scanning lines. Further, the B-mode processing circuitry 13 extracts the harmonic component by performing an adding/subtracting process corresponding to a modulation method on the plurality of pieces of reflected-wave data (the reception signals) corresponding to the scanning lines. After that, the B-mode processing circuitry 13 generates B-mode data by performing the envelope detecting process or the like on the reflected-wave data (the reception signals) of the harmonic component.

For example, when the PM method is implemented, according to a scan sequence set by the processing circuitry 18, the transmission and reception circuit 11 causes ultrasound waves having opposite phase polarities and mutually the same amplitude levels (e.g., −1 and 1) to be transmitted twice for each of the scanning lines. Further, the transmission and reception circuit 11 generates a reception signal resulting from the transmission corresponding to "−1" and another reception signal resulting from the transmission corresponding to "1", so that the B-mode processing circuitry 13 adds the two reception signals together. As a result, a signal is generated from which the fundamental wave component has been eliminated and in which a second harmonic component primarily remains. Further, the B-mode processing circuitry 13 generates THI B-mode data and/or CHI B-mode data by performing an envelope detecting process or the like on the generated signal.

Alternatively, for example, for THI processes, a method has been put into practical use by which images are rendered while using the second harmonic component included in the reception signal and a combination tone component. According to an image rendering method that uses the combination tone component, for example, the ultrasound probe 1 is caused to transmit a transmission ultrasound wave having a combined waveform obtained by combining together a first fundamental wave of which the center frequency is equal to "f1" and a second fundamental wave of which the center frequency is equal to "f2" that is higher than "f1". The combined waveform is a waveform obtained by combining together the waveform of the first fundamental wave and the waveform of the second fundamental wave, while the phases of the two waveforms are adjusted so as to generate the combination tone component having the same polarity as that of the second harmonic component. The transmission and reception circuit 11 causes the transmission ultrasound wave having the combined waveform to be transmitted twice, for example, while inverting the phase thereof. In that situation, for example, by adding the two reception signals together, the B-mode processing circuitry 13 extracts a harmonic component from which the fundamental wave component has been eliminated and in which the combination tone component and the second harmonic component primarily remain, and subsequently performs the envelope detecting process or the like.

By performing a frequency analysis on the reflected-wave data read from the buffer 12, the Doppler processing circuitry 14 is configured to generate data (Doppler data) obtained by extracting movement information based on a Doppler effect about moving members that are present in a scan range. More specifically, as the movement information of the moving members, the Doppler processing circuitry 14 generates Doppler data with respect to each of multiple sampling points, on the basis of an average velocity value, an average dispersion value, an average power value, and/or the like. In this situation, the moving members may be, for example, a blood flow, a tissue such as the cardiac wall, and a contrast agent. The movement information of the moving members may also be referred to as moving member information. As the movement information of a blood flow (blood flow information), the Doppler processing circuitry 14 according to the present embodiment generates the Doppler data obtained by speculating an average velocity value of the blood flow, a dispersion value of blood flow velocity values, a power value of a blood flow signal, and/or the like, with respect to each of the multiple sampling points.

By using the abovementioned function of the Doppler processing circuitry 14, the ultrasound diagnosis apparatus according to the present embodiment is capable of implementing a color Doppler method that may also be called a Color Flow Mapping (CFM) method. According to the CFM method, the transmission and reception of an ultrasound wave is performed multiple times on a plurality of scanning lines. Further, according to the CFM method, by applying a Moving Target Indicator (MTI) filter to a data sequence of mutually the same position, a signal derived from a blood flow is extracted, while suppressing a signal (a clutter signal) derived from stationary or slowly-moving tissues. Further, according to the CFM method, on the basis of the blood flow signal, the blood flow information such as a velocity value of the blood flow, a dispersion value of the blood flow, a power value of the blood flow, and/or the like are speculated. The image generating circuit 15 (explained later) is configured to generate ultrasound image data (color Doppler image data) two-dimensionally displaying a distribution of results of the speculation in color, for example. Further, the display 2 is configured to display the color Doppler image data.

Generally speaking, as MTI filters, filters having a fixed coefficient such as Butterworth Infinite Impulse Response (IIR) filters and polynomial regression filters are usually used. In contrast, as the MTI filter, the Doppler processing circuitry 14 according to the present embodiment is configured to use an adaptive MTI filter of which the coefficient is varied in accordance with an input signal. More specifically, as the adaptive MTI filter, the Doppler processing circuitry 14 according to the present embodiment is configured to use a filter called "eigenvector regression filter". In the following sections, the "eigenvector regression filter" realized with an adaptive MTI filter using eigenvectors will be referred to as an "eigenvector MTI filter".

The eigenvector MTI filter is configured to calculate eigenvectors on the basis of a correlation matrix and to further calculate a coefficient to be used in the clutter component suppressing process on the basis of the calculated eigenvectors. This method is an application of methods used in principal component analyses, Karhunen-Loeve transform schemes, and eigenspace schemes.

As illustrated in FIG. 1, the Doppler processing circuitry 14 according to the first embodiment that employs the eigenvector MTI filter is configured to execute: a correlation matrix calculating function 141, a calculating function 142, an MTI filter processing function 143, a speculating function 144, a saturation speculating function 145, and a blank filling function 146. In this situation, for example, the processing functions executed by the constituent elements of the Doppler processing circuitry 14 illustrated in FIG. 1, namely, the correlation matrix calculating function 141, the calculating function 142, the MTI filter processing function 143, the speculating function 144, the saturation speculating function 145, and the blank filling function 146 are each recorded in the internal storage circuit 17 in the form of a computer-executable program. For example, the Doppler processing circuitry 14 is a processor and is configured to read the programs from the internal storage circuit 17 and to realize the functions corresponding to the read programs by executing the read programs. In other words, the Doppler processing circuitry 14 that has read the programs has the functions illustrated within the Doppler processing circuitry 14 in FIG. 1.

The correlation matrix calculating function 141 is configured to calculate a correlation matrix of the scan range from a data sequence of sequential pieces of reflected-wave data in mutually the same position (mutually the same sampling point). In other words, the correlation matrix calculating function 141 is configured to calculate the correlation matrix as a statistical characteristic, by using the data sequence represented by a set made up of output signals. For example, the calculating function 142 is configured to calculate eigenvalues of the correlation matrix and eigenvectors corresponding to the calculated eigenvalues.

For example, the calculating function 142 calculates, as a filter matrix used for suppressing the clutter component, a matrix obtained by reducing the rank of the matrix in which the eigenvectors are arranged on the basis of the magnitudes of the eigenvalues. In other words, the calculating function 142 is configured to calculate a filter coefficient used for suppressing the clutter component, on the basis of a result of a principal component analysis performed by using the correlation matrix.

By using the filter matrix, the MTI filter processing function 143 is configured to output a data sequence obtained by extracting a blood flow signal derived from the blood flow while suppressing the clutter component, from the data sequence of the sequential pieces of reflected-wave data in mutually the same position (mutually the same sampling point).

The speculating function 144 is configured to speculate blood flow information by performing a calculation such as an autocorrelation calculation while using the data output by the MTI filter processing function 143 and to further output the speculated blood flow information as Doppler data. In other words, the speculating function 144 extracts the moving member information by using the filter coefficient on the basis of the data sequence. In this situation, the correlation matrix calculating function 141, the calculating function 142, the MTI filter processing function 143, and the speculating function 144 are examples of an extracting unit.

The saturation speculating function 145 is configured to speculate saturation of the reflected-wave signals observed before the phased addition process performed by using the reflected-wave signals, in accordance with the intensity of the reflected-wave data generated through the phased addition process, the reflected-wave signals being generated by transmitting an ultrasound wave with respect to mutually the same scanning line, and the saturation speculating function 145 is configured to further output a result of the speculation. For example, the saturation speculating function 145 outputs an output signal based on the result of the speculation. In one example, when at least one of the pieces of packet data corresponding to the output position exhibits an amplitude level exceeding a threshold value, the saturation speculating function 145 performs a process of arranging all the pieces of packet data to be 0. The saturation speculating function 145 is an example of a saturation speculating unit.

With respect to an observation point at which the reflected-wave signal observed before the phased addition process is speculated to be saturated, the blank filling function 146 is configured to interpolate moving member information in the surroundings of the observation point into the moving member information of the observation point. For example, the blank filling function 146 fills the blank in a location where the power value became 0 after the saturation speculating function 145 detects saturation, by using the data in the surroundings thereof. In one example, the blank filling function 146 outputs an average value of neighboring pieces of data that are not 0. The blank filling function 146 is an example of an interpolating unit. Further, specific processes performed by the Doppler processing circuitry 14 according to the first embodiment will be explained in detail later.

The B-mode processing circuitry 13 and the Doppler processing circuitry 14 illustrated in FIG. 1 are capable of processing both two-dimensional reflected-wave data and three-dimensional reflected-wave data. In other words, the B-mode processing circuitry 13 is configured to generate two-dimensional B-mode data from the two-dimensional reflected-wave data and to generate three-dimensional B-mode data from the three-dimensional reflected-wave data. Further, the Doppler processing circuitry 14 is configured to generate two-dimensional Doppler data from the two-dimensional reflected-wave data and to generate three-dimensional Doppler data from the three-dimensional reflected-wave data.

The image generating circuit 15 is configured to generate the ultrasound image data from the data generated by the B-mode processing circuitry 13 and the Doppler processing circuitry 14. The image generating circuit 15 is configured to generate two-dimensional B-mode image data in which the intensities of reflected waves are expressed with degrees of brightness, from the two-dimensional B-mode data generated by the B-mode processing circuitry 13. Further, the image generating circuit 15 is configured to generate two-dimensional Doppler image data in which the blood flow information is rendered in an image from the two-dimensional Doppler data generated by the Doppler processing circuitry 14. In other words, the image generating circuit 15 is configured to generate the image data based on the moving member information. The two-dimensional Doppler image data may be velocity image data, dispersion image data, power image data or image data combining any of these. As the Doppler image data, the image generating circuit 15 is configured to generate color Doppler image data in which the blood flow information is displayed in color and to generate Doppler image data in which a certain piece of blood flow information is displayed on a gray scale.

In this situation, generally speaking, the image generating circuit 15 converts (by performing a scan convert process) a scanning line signal sequence from an ultrasound scan into a scanning line signal sequence in a video format used by, for example, television and generates display-purpose ultrasound image data. More specifically, the image generating circuit 15 generates the display-purpose ultrasound image data by performing a coordinate transformation process compliant with the ultrasound scanning mode used by the ultrasound probe 1. Further, as various types of image processing processes besides the scan convert process, the image generating circuit 15 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuit 15 combines text information of various parameters, scale graduations, body marks, and the like with the ultrasound image data.

In other words, the B-mode data and the Doppler data are each ultrasound image data before the scan convert process. The data generated by the image generating circuit 15 is the display-purpose ultrasound image data after the scan convert process. The B-mode data and the Doppler data may each also be referred to as "raw data". The image generating circuit 15 generates the display-purpose two-dimensional ultrasound image data from the two-dimensional ultrasound image data before the scan convert process.

Further, the image generating circuit 15 is configured to generate three-dimensional B-mode image data by performing a coordinate transformation process on the three-dimensional B-mode data generated by the B-mode processing circuitry 13. Further, the image generating circuit 15 is configured to generate three-dimensional Doppler image data by performing a coordinate transformation process on the three-dimensional Doppler data generated by the Doppler processing circuitry 14. The image generating circuit 15 is configured to generate the "three-dimensional B-mode image data and three-dimensional Doppler image data" each as "three-dimensional ultrasound image data (volume data)".

Further, for the purpose of generating various types of two-dimensional image data used for causing the display 2 to display the volume data, the image generating circuit 15 is configured to perform a rendering process on the volume data. Examples of the rendering process performed by the image generating circuit 15 includes a process of generating Multi Planar Reconstruction (MPR) image data from the volume data by implementing an MPR method. Further, another example of the rendering process performed by the image generating circuit 15 is a Volume Rendering (VR) process by which two-dimensional image data reflecting three-dimensional information is generated. The image generating circuit 15 is an example of an image generating unit.

The image memory 16 is a memory configured to store therein the display-purpose image data generated by the image generating circuit 15. Further, the image memory 16 is also capable of storing therein any of the data generated by the B-mode processing circuitry 13 and the Doppler processing circuitry 14. After a diagnosis process, for example, the operator is able to invoke any of the B-mode data and the Doppler data stored in the image memory 16. The invoked B-mode data and Doppler data can serve as display-purpose ultrasound image data after being routed through the image generating circuit 15. Further, the image memory 16 is also capable of storing therein the reflected-wave data output by the transmission and reception circuit 11.

The internal storage circuit 17 is configured to store therein control programs for performing ultrasound transmissions and receptions, image processing processes, and display processes as well as various types of data such as diagnosis information (e.g., patient's IDs, medical doctors' observations), diagnosis protocols, various types of body marks, and the like. Further, the internal storage circuit 17 may be used, as necessary, for saving therein any of the image data stored in the image memory 16, and the like. Further, the data stored in the internal storage circuit 17 may be transferred to an external apparatus via an interface (not illustrated). Further, the internal storage circuit 17 is also capable of storing therein data transferred thereto from an external apparatus via an interface (not illustrated).

The processing circuitry 18 is configured to control the overall processes performed by the ultrasound diagnosis apparatus. More specifically, the processing circuitry 18 is configured to control processes performed by the transmission and reception circuit 11, the B-mode processing circuitry 13, the Doppler processing circuitry 14, and the image generating circuit 15, on the basis of the various types of setting requests input by the operator via the input device 3 and the various types of control programs and the various types of data read from the internal storage circuit 17. For example, the processing circuitry 18 is configured to control an ultrasound scan, by controlling the ultrasound probe 1 via the transmission and reception circuit 11. Normally, according to the CFM method, together with color Doppler image data represented by blood flow image data, B-mode image data represented by tissue image data is displayed. To realize the display in this manner, the processing circuitry 18 causes the ultrasound probe 1 to perform the first ultrasound scan to obtain the blood flow information in the first scan range. For example, the first ultrasound scan is an ultrasound scan performed for acquiring color Doppler image data in a Doppler mode. Further, together with the first ultrasound scan, the processing circuitry 18 causes the ultrasound probe 1 to perform the second ultrasound scan to obtain information about the shapes of the tissues in the second scan range. For example, the second ultrasound scan is an ultrasound scan performed for acquiring B-mode image data in a B-mode.

The processing circuitry 18 causes the first ultrasound scan and the second ultrasound scan to be performed, by controlling the ultrasound probe 1 via the transmission and reception circuit 11. As for the first scan range and the second scan range, the two scan ranges may be the same as each other. Alternatively, the first scan range may be smaller than the second scan range. Conversely, the second scan range may be smaller than the first scan range.

Further, the processing circuitry 18 is configured to exercise control so that the display 2 displays any of the display-purpose ultrasound image data stored in the image memory 16 and the internal storage circuit 17. The transmission and reception circuit 11 and the like built in the apparatus main body 10 may be configured by using hardware such as an integrated circuit or may be configured as a modularized program by using software. The processing circuitry 18 is an example of a controlling unit.

An overall configuration of the ultrasound diagnosis apparatus according to the first embodiment has thus been explained. The ultrasound diagnosis apparatus according to the first embodiment structured as described above is configured to implement the CFM method by using the blood flow information (the Doppler data) speculated by using the eigenvector MTI filter. As explained above, the Doppler processing circuitry 14 employing the eigenvector MTI filter is configured to calculate the eigenvectors from the correlation matrix.

Incidentally, when the CFM method employing the eigenvector MTI filter is implemented by transmitting a plane wave or a diffuse wave, there is a problem where, when signals become saturated, an arc-shaped artifact may occur due to an increase of a side lobe. As a countermeasure for this problem, a method is known by which a saturation detecting process is performed on channel signals (hereinafter, "CH signals") observed before the beam forming process, for example. It is, however, difficult to realize this method. For example, most of the beam formers that are currently used are configured by using hardware. We are therefore not in an environment where beam formers can freely be controlled by using software. Further, when actually realizing a beam former by using hardware, an increase in the circuit scale can be a problem. Further, when the saturation detecting process and the beam forming process are performed by using software, another problem may arise where the load imposed on the software becomes large, and real-timeness thereof may be impeded.

Figure 2:
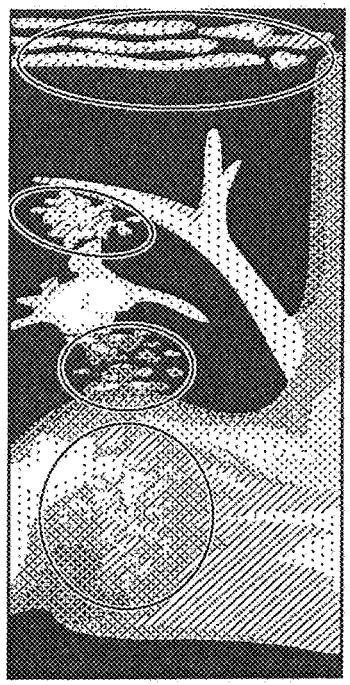
FIG. 2 is a drawing for explaining a comparison example.

In contrast, as a comparison example, when the CFM method employing the eigenvector MTI filter is implemented while applying a transmission focus, no arc-shaped artifact is observed because the side lobe from the transmission and reception is suppressed. FIG. 2 is a drawing for explaining the comparison example. FIG. 2 illustrates an example in which, while the CFM method employing the eigenvector MTI filter is implemented by applying a transmission focus, power values of a blood flow are rendered in an image. No arc-shaped artifact is exhibited in FIG. 2. Accordingly, there seems to be no impact from saturated signals.

However, in the presence of a powerful reflecting member, when reflected-wave signals reflected by the powerful reflecting member become saturated, a problem arises where an image is displayed as if there was a blood flow in the location where the powerful reflecting member is present. For example, in FIG. 2, a powerful reflecting member is present in the circled regions. Accordingly, in the image illustrated in FIG. 2, there is a risk that something that is not actually a blood flow may be mistakenly recognized as a blood flow during diagnosis processes, which may cause a serious clinical problem. In other words, a side lobe caused by saturation from a powerful reflecting member is evidently displayed as an arc-shaped artifact and is thus recognizable. In contrast, saturation in a main lobe does not occur as an arc-shaped artifact, and the impact on the entire image is latent and is thus unrecognizable.

The inventors of the present disclosure have discovered that, even when there seems to be no impact of the saturated signals at a glance as described above, the saturated signals can impact the correlation matrix and may exert a bad influence on an entire image by hindering the generation of an optimal MTI filter matrix. To cope with this situation, in the following sections, a medical image processing method will be explained with which it is possible to alleviate impacts the saturation of a main lobe, while implementing the CFM method employing an eigenvector MTI filter and applying a transmission focus. For example, the medical image processing method includes: speculating saturation of reflected-wave signals observed before the phased addition process performed by using the reflected-wave signals, in accordance with the intensity of the reflected-wave data generated through the phased addition process, the reflected-wave signals being generated by transmitting an ultrasound wave with respect to mutually the same scanning line; and outputting a result of the speculation. After that, the data based on the result of the speculation is displayed on the display 2. The medical image processing method is realized as a result of the Doppler processing circuitry 14 executing the correlation matrix calculating function 141, the calculating function 142, the MTI filter processing function 143, the speculating function 144, the saturation speculating function 145, and the blank filling function 146.

Figure 3:
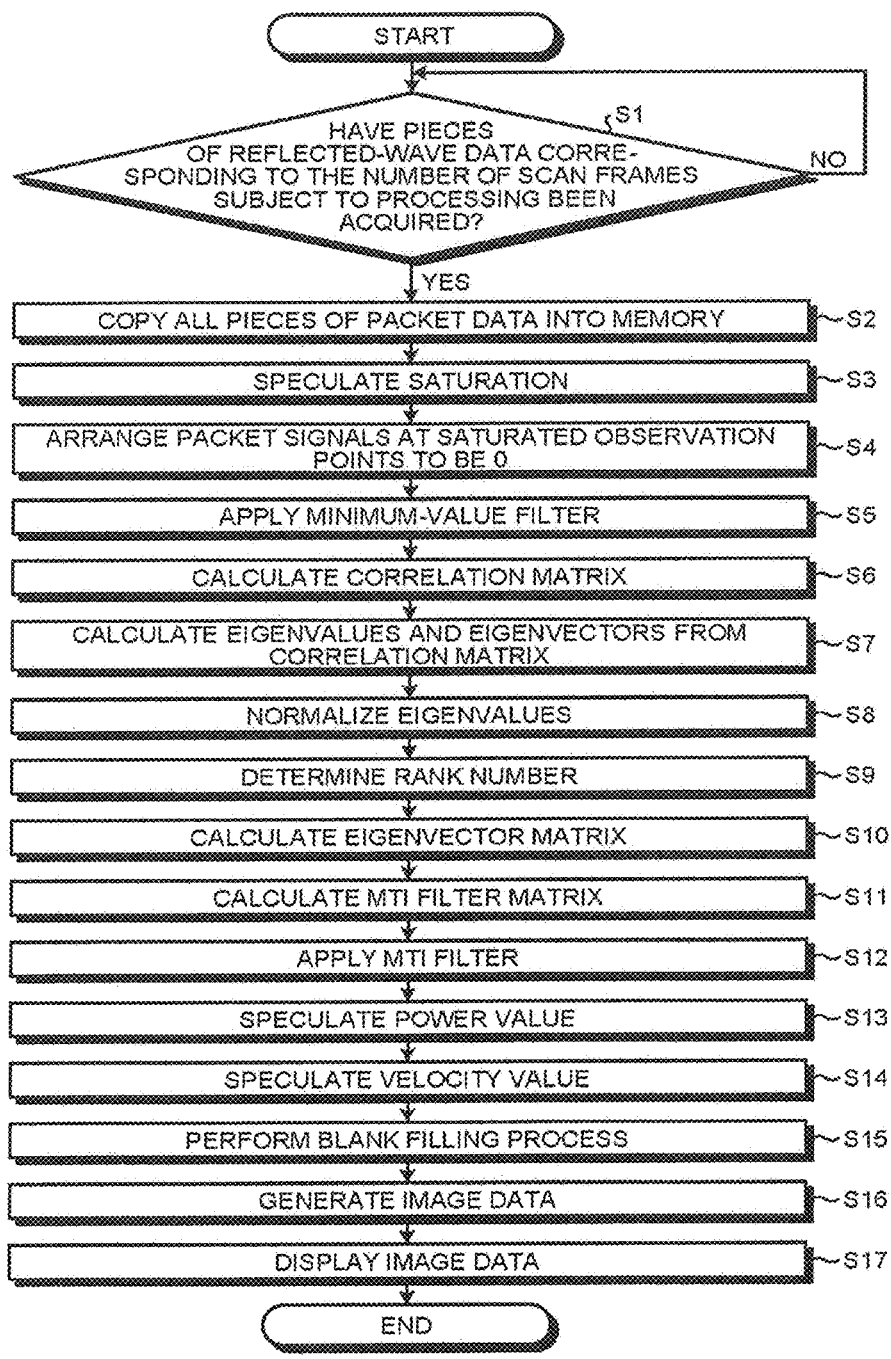
FIG. 3 is a flowchart illustrating a processing procedure performed by the ultrasound diagnosis apparatus according to the first embodiment.

FIG. 3 is a flowchart illustrating a processing procedure performed by the ultrasound diagnosis apparatus according to the first embodiment. With reference to FIG. 3, which step in the flowchart corresponds to each of the constituent elements of the ultrasound diagnosis apparatus will be explained.

Steps S1 through S5 are steps corresponding to the saturation speculating function 145. Steps S1 through S5 are steps at which the saturation speculating function 145 is realized as a result of the Doppler processing circuitry 14 invoking and executing a predetermined program corresponding to the saturation speculating function 145 from the internal storage circuit 17. At step S1, the saturation speculating function 145 judges whether or not pieces of reflected-wave data corresponding to the number of scan frames subject to the processing have been acquired (step S1). In this situation, when having determined that the pieces of reflected-wave data corresponding to the number of scan frames have not been acquired (step S1: No), the saturation speculating function 145 repeatedly performs the judging process at step S1.

On the contrary, when having determined that the pieces of reflected-wave data corresponding to the number of scan frames have been acquired (step S1: Yes), the saturation speculating function 145 proceeds to step S2. At step S2, the saturation speculating function 145 copies all the pieces of packet data corresponding to all the spatial points into a memory. In this situation, the number of all the spatial points will be expressed as N, whereas the packet size will be expressed as L. For example, the saturation speculating function 145 copies the input data within the buffer 12 into a memory provided within the Doppler processing circuitry 14. In other words, the saturation speculating function 145 does not rewrite the input data in the buffer 12. The saturation speculating function 145 performs the abovementioned copying operation for each invoked packet.

At step S3, the saturation speculating function 145 speculates saturation. For example, in accordance with the intensity of the reflected-wave data generated through the phased addition process performed by using the reflected-wave signals generated by transmitting an ultrasound wave with respect to mutually the same scanning line, the saturation speculating function 145 speculates saturation of the reflected-wave signals observed before the phased addition process. In this situation, when the amplitude level of the IQ signals indicated in Expression (1) presented below is equal to or larger than a threshold value, or when the power value indicated in Expression (2) presented below is equal to or larger than a threshold value, the saturation speculating function 145 speculates that the signals are saturated. It is desirable to set the threshold value to be in the range of approximately 50% to 70% of the maximum value of the amplitude of the IQ signals. Alternatively, instead of examining the amplitude level or the power value, the saturation speculating function 145 may speculate that the signals are saturated when one of the absolute values of I and Q exceeds a threshold value.

$$\sqrt{I^2+Q^2} \tag{1}$$

$$I^2+Q^2 \tag{2}$$

At step S4, the saturation speculating function 145 arranges packet signals at saturated observation points to be 0. For example, when at least one of the packets in mutually the same location point exhibits saturated signals, the saturation speculating function 145 arranges all the packet signals to be 0. In other words, when having speculated that one or more reflected-wave signals observed before the phased addition process are saturated, the saturation speculating function 145 outputs an output signal obtained by multiplying the reflected-wave data by 0.

Incidentally, it is impossible to correctly detect after the beam forming process whether or not the input signals corresponding to the channels [CH] became saturated in the A/D converter [ADC]. However, in the present example, it is sufficient when we are able to roughly find out whether the signals of the main lobe are saturated or not. The reason is that, in the correlation matrix calculated later, signals having larger amplitude levels are dominant. If the dominant signals having larger amplitude levels were contained in a packet while being may be saturated and may be unsaturated, it would be impossible to calculate a correct MTI filter matrix. For this reason, the saturation speculating function 145 excludes these signals from the calculation by arranging all the elements to be 0.

At step S5, the saturation speculating function 145 applies a minimum-value filter. For example, when a saturated signal is present in an area of a kernel size within a spatial region, the saturation speculating function 145 applies a filter that arranges all the signals in the area of the kernel size to be 0. In this situation, an example of the filter may be a minimum-value filter having a kernel size of 3×3 (three samples in the distance direction by three rasters in the raster direction). A side lobe occurs in the vicinity of the location detected to be saturated due to an impact of the saturated channel [CH]. Thus, the minimum-value filter is used for the purpose of eliminating such an impact. In other words, when having speculated that one or more reflected-wave signals observed before the phased addition process are saturated at any of the observation points, the saturation speculating function 145 outputs an output signal obtained by multiplying the data by 0, with respect to the space in the vicinity of the observation point. Alternatively, when having speculated that one or more reflected-wave signals observed before the phased addition process are saturated at any of the observation points, the saturation speculating function 145 may output an output signal obtained by multiplying the data by a predetermined coefficient having a value smaller than 1, with respect to the space in the vicinity of the observation point.

Step S6 is a step corresponding to the correlation matrix calculating function 141. Step S6 is a step at which the correlation matrix calculating function 141 is realized as a result of the Doppler processing circuitry 14 invoking and executing a predetermined program corresponding to the correlation matrix calculating function 141 from the internal storage circuit 17. At step S6, the correlation matrix calculating function 141 calculates a correlation matrix Rxx by calculating an ensemble average of all the location points.

In this situation, when a packet data column vector at a certain location point i is expressed as $x_i$, it is possible to express the correlation matrix $R_{xx}$ by using Expression (3) presented below. In Expression (3), i denotes the position of the certain location point. (The single subscript i denotes the position of x,z for a two-dimensional scan and the position of x,y,z for a three-dimensional scan.) N denotes the number of location points used for the calculation. The symbol "*" denotes a complex conjugate transpose matrix (a Hermitian transpose matrix). $R_{xx}$ can be expressed as a matrix of L×L.

$$R_{xx} = \frac{1}{N}\sum_{i=1}^{N} x_i x_i^* \qquad (3)$$

Steps S7 through S11 are steps corresponding to the calculating function 142. Steps S7 through S11 are steps at which the calculating function 142 is realized as a result of the Doppler processing circuitry 14 invoking and executing a predetermined program corresponding to the calculating function 142 from the internal storage circuit 17. At step S7, the calculating function 142 calculates eigenvalues and eigenvectors from the correlation matrix. In this situation, the calculating function 142 calculates an eigenvector matrix V and an eigenvalue matrix D by performing an eigenvalue decomposition on $R_{xx}$. It is possible to express the eigenvalue decomposition performed on $R_{xx}$ by using Expression (4) presented below.

$$R_{xx} = VDV^* \qquad (4)$$

In Expression (4) above, V denotes a matrix having eigenvectors as the column vectors thereof. D denotes a diagonal matrix having eigenvalues as diagonal elements thereof. It is assumed that the eigenvalues λ and eigenvectors corresponding to the eigenvalues λ are each arranged in descending order. The matrix V can be expressed by using Expression (5) presented below. The matrix D can be expressed by using Expression (6) presented below.

$$V = \begin{pmatrix} v_{1,1} & v_{1,2} & \cdots & v_{1,L} \\ v_{2,1} & v_{2,2} & & v_{2,L} \\ \vdots & & & \vdots \\ v_{L,1} & v_{L,2} & \cdots & v_{L,L} \end{pmatrix} \qquad (5)$$

$$D = \begin{pmatrix} \lambda_1 & 0 & \cdots & 0 \\ 0 & \lambda_2 & & 0 \\ \vdots & & \ddots & \vdots \\ 0 & 0 & \cdots & \lambda_L \end{pmatrix} \qquad (6)$$

At step S8, the calculating function 142 normalizes the eigenvalues by using the largest eigenvalue $\lambda_1$, while using Expression (7) presented below.

$$\lambda_i = \lambda_i/\lambda_1 \; (i=1,\ldots,L) \qquad (7)$$

At step S9, the calculating function 142 calculates an optimal rank cut number k from the eigenvalues. The calculating function 142 may calculate the optimal rank cut number k by using a method disclosed in Patent Literature 1 (Japanese Patent Laid-open No. 2014-158698) or as the smallest value that makes $\lambda_k$ equal to or smaller than a threshold value. By normalizing the eigenvalues with the largest eigenvalue λ1 at step S8 before making the comparison with the threshold value at step S9, it is possible to eliminate impacts of gains.

At step S10, by using the value of k (where k≤L) calculated above, the calculating function 142 calculates an eigenvector matrix $V_k$ (an L×K matrix) of which the rank number is k. In this situation, it is possible to express the eigenvector matrix $V_k$ by using Expression (8) presented below.

$$V_k = \begin{pmatrix} v_{1,1} & v_{1,2} & \cdots & v_{1,k} \\ v_{2,1} & v_{2,2} & & v_{2,k} \\ \vdots & & & \vdots \\ v_{L,1} & v_{L,2} & \cdots & v_{L,k} \end{pmatrix} \qquad (8)$$

At step S11, the calculating function 142 calculates an MTI filter matrix W from $V_k$. In Expression (9), I denotes a unit matrix of L×L.

$$W = I - V_k V_k^* \qquad (9)$$

Step S12 is a step corresponding to the MTI filter processing function 143. Step S12 is a step at which the MTI filter processing function 143 is realized as a result of the Doppler processing circuitry 14 invoking and executing a predetermined program corresponding to the MTI filter processing function 143 from the internal storage circuit 17. At step S12, the MTI filter processing function 143 applies an MTI filter to the packet column vector data $x_i$ at each of the points by using Expression (10) presented below. In this situation, the MTI filter processing function 143 performs an MTI filter processing process by receiving an input of the data resulting from the process performed by the saturation speculating function 145.

$$y_i = W x_i \qquad (10)$$

Steps S13 and S14 are steps corresponding to the speculating function 144. Steps S13 and S14 are steps at which the speculating function 144 is realized as a result of the Doppler processing circuitry 14 invoking and executing a predetermined program corresponding to the speculating function 144 from the internal storage circuit 17. At steps S13 and S14, the speculating function 144 extracts moving member information by using the result of the MTI filter processing process at step S12. In other words, the speculating function 144 extracts the moving member information by using a statistical characteristic, on the basis of the data sequence represented by a set made up of the output signals. More specifically, at step S13, the speculating function 144 speculates a power value P, by using Expression (11) presented below. In this situation, the speculating function 144 speculates the power value P as a value before a logarithmic compression. In Expression (11), j denotes an index indicating an element number of the column vector.

$$P_i = \sum_{j=1}^{L} |y_{i,j}|^2 \quad (11)$$

Further, at step S14, the speculating function 144 speculates a velocity value V by using Expression (12) presented below. In Expression (12), "angle" denotes a mathematical function used for outputting the argument of a complex number in the range from $-\pi$ to $\pi$.

$$V_i = \text{angle}\left(\sum_{j=1}^{L-1} y_{i,j}^* y_{i,j+1}\right) \quad (12)$$

In this manner, the speculating function 144 extracts the moving member information based on the result of the speculation performed by the saturation speculating function 145. In other words, when the saturation speculating function 145 has output an output signal indicating that one or more reflected-wave signals observed before the phased addition process are speculated to be saturated, the speculating function 144 arranges the output signal not to be used for the extraction of the moving member information. In this situation, the speculating function 144 may perform the processes at steps S13 and S14 in the reverse order or at the same time.

Step S15 is a step corresponding to the blank filling function 146. Step S15 is a step at which the blank filling function 146 is realized as a result of the Doppler processing circuitry 14 invoking and executing a predetermined program corresponding to the blank filling function 146 from the internal storage circuit 17. At step S15, the blank filling function 146 executes a blank filling process. In this situation, for example, the power value P and the velocity value V in the position where 0 was entered by the saturation speculating function 145 are each 0. Accordingly, the blank filling function 146 fills in the blanks of the power value P and the velocity value P being 0 using the data in the surroundings thereof. In one example, the blank filling function 146 outputs an average value of neighboring pieces of data that are not 0. More specifically, the blank filling function 146 outputs an average value of pieces of data in the 3×3 positions centered on the position indicated as 0. The process at step S15 performed by the blank filling function 146 may be omitted as appropriate.

Step S16 is a step realized by the image generating circuit 15. At step S16, the image generating circuit 15 generates color Doppler image data from the moving member information. For example, the image generating circuit 15 generates the color Doppler image data by performing a logarithmic compression on the power value P speculated at step S13. Further, the image generating circuit 15 generates color Doppler image data based on the velocity value V speculated at step S14.

Figure 4:
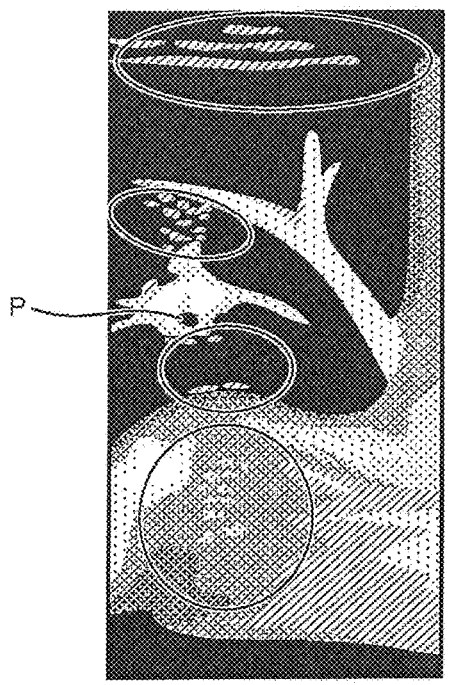
FIG. 4 is a drawing for explaining the first embodiment.

Step S17 is a step realized by the processing circuitry 18. At step S17, the processing circuitry 18 causes the display 2 to display the color Doppler image data, as data based on the result of the signal saturation speculating process. FIG. 4 is a drawing for explaining the first embodiment. FIG. 4 illustrates an example in which blood flow power values are rendered in an image by generating an eigenvector MTI filter in such a manner that when the IQ signals observed after the beam forming process at a certain observation point are equal to or higher than a threshold value, all the pieces of packet data at the observation point are arranged to be 0 and implementing the CFM method while using the eigenvector MTI filter. For the sake of convenience in the explanation, FIG. 4 illustrates an image for which the gain is arranged to be larger than the gain in the image in FIG. 2. If the gain were the same, the brightness levels of the blood flow would be the same. Accordingly, it is observed from FIG. 4 that the tissues are significantly reduced compared to that in FIG. 2. For example, in the regions circled in FIG. 4, tissues in the body surface layer and parenchyma are significantly suppressed compared to those in the image in FIG. 2.

Further, FIG. 4 illustrates the image without the blank filling process so as to indicate the positions where 0 was entered due to saturation. For example, in FIG. 4, the parts that are dark and missing represent observation points P speculated to have saturation. Although the example in FIG. 4 has only few observation points P speculated to have saturation, the image is significantly different. The reason is that correlation matrices are greatly impacted by signals having large amplitude. Because the levels of the signals speculated to be saturated are high, those signals greatly impact the correlation matrices. Further, the packet sequence containing a signal speculated to be saturated does not exhibit correct information. In FIG. 2, because a correct MTI filter matrix is not generated, clutter is left in the entire image. In contrast, in the example in FIG. 4, because the MTI filter matrix is calculated by using the data from which the saturated parts have been eliminated in advance, an excellent image is displayed. As explained herein, by simply eliminating the saturated observation points P that are very few, it is possible to improve the image quality of the blood flow image as observed in the change from FIG. 2 to FIG. 4.

As explained above, the ultrasound diagnosis apparatus according to the first embodiment is configured to speculate the saturation at each of the observation points in accordance with the intensity of the reflected-wave data generated through the phased addition process and to further calculate the correlation matrix of the entire imaging target area by using the output result in which the signals at the observation points speculated to have saturation are suppressed. With these arrangements, according to the first embodiment, it is possible to reduce the impacts of the saturated signals imposed on the correlation matrix. Further, the ultrasound diagnosis apparatus according to the first embodiment is configured to generate the MTI filter from the correlation matrix in which the impacts of the saturated signals have been reduced. It is therefore possible to alleviate the occurrence of the problem where an image may be displayed as if there was a blood flow in a part where a powerful reflecting member is present.

In the first embodiment above, the example is explained in which the MTI filter processing function 143 is configured to perform the MTI filter processing process by receiving the input of the data processed by the saturation speculating function 145; however, possible embodiments are not limited to this example. For instance, the MTI filter processing function 143 may perform the MTI filter processing process by receiving an input of data that has not been processed by the saturation speculating function 145. In that situation, the Doppler processing circuitry 14 does not necessarily have to execute the blank filling function 146.

A Modification Example of First Embodiment

In the first embodiment described above, the example is explained in which the Doppler processing circuitry 14 is configured to calculate the correlation matrix as a statistical characteristic and performs the eigenvalue decomposition. As a modification example of the first embodiment, an example will be explained in which, instead of calculating the correlation matrix, a singular value decomposition is performed on a matrix X* to obtain a statistical characteristic. For example, when the number of all the spatial points is expressed as N, while the packet size is expressed as L, it is possible to express Expression (3) presented above with Expression (13) presented below, by using a matrix X of L×N where the column vectors of the matrix X are xi.

$$R_{xx} = \frac{1}{N} XX^* \qquad (13)$$

The Doppler processing circuitry 14 performs a singular value decomposition on the matrix X*, by using Expression (14) presented below.

$$X^* = P\Lambda Q^* \qquad (14)$$

When Expression (14) is assigned to Expression (13), because P is a unitary matrix, it is possible to express $R_{xx}$ by using Expression (15) presented below.

$$R_{xx} = \frac{1}{N} XX^* = \frac{1}{N}(P\Lambda Q^*)^*(P\Lambda Q^*) = \frac{1}{N}Q\Lambda^* P^* P\Lambda Q^* = \frac{1}{N}Q\Lambda^* \Lambda Q^* \qquad (15)$$

When Expression (4) is compared with Expression (15), it is possible to express V by using Expression (16) presented below and to express D by using Expression (17) presented below.

$$V = Q \qquad (16)$$

$$D = \frac{1}{N}\Lambda^* \Lambda \qquad (17)$$

In Expression (17), $\Lambda$ is a matrix of N×L, while the eigenvalues of the Hermitian matrix $R_{xx}$ are positive. Accordingly, it is possible to express $\Lambda$ by using Expression (18) presented below.

$$\Lambda = \sqrt{N} \begin{pmatrix} \sqrt{\lambda_1} & 0 & \cdots & 0 \\ 0 & \sqrt{\lambda_1} & & 0 \\ \vdots & & \ddots & \vdots \\ 0 & 0 & \cdots & \sqrt{\lambda_L} \\ 0 & 0 & \cdots & 0 \\ \vdots & \vdots & \ddots & \vdots \\ 0 & 0 & \cdots & 0 \end{pmatrix} \qquad (18)$$

In that situation, the MTI filter processing function 143 applies an MTI filter to the packet column vector data X at each of the points, by using Expression (19) presented below.

$$Y = WX \qquad (19)$$

As explained above, in the modification example of the first embodiment, the Doppler processing circuitry 14 is configured to extract the moving member information by performing the singular value decomposition on the matrix X* instead of calculating the correlation matrix.

Second Embodiment

Figure 5:
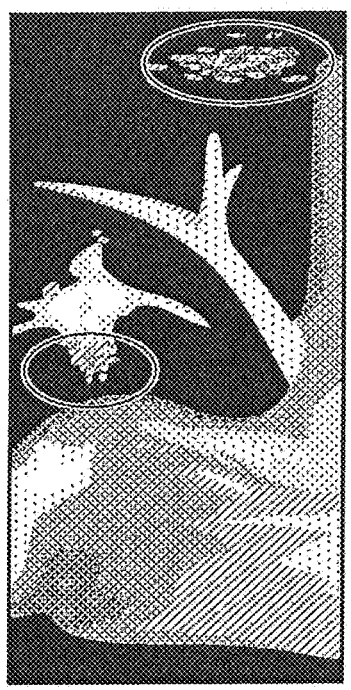
FIG. 5 is a drawing for explaining another comparison example.

In the first embodiment, the example is explained in which the single correlation matrix is calculated for the entire imaging target area from the output signal based on the result of the saturation speculating process. Incidentally, a method is known by which an image is separated into two or more regions, so as to apply an MTI filter by calculating a correlation matrix and an MTI filter matrix for each of the sectional regions. FIG. 5 is a drawing for explaining a comparison example.

FIG. 5 illustrates an example in which power values of a blood flow are rendered in an image by implementing the CFM method while employing an eigenvector MTI filter for each of the regions and applying a transmission focus. More specifically, in FIG. 5, the imaging target area is separated into the two or more regions in such a manner that parts thereof overlap with one another, so as to calculate correlation matrices and MTI filter matrices and to perform weighted addition on power signals in an output of the MTI filter. In the example in FIG. 5, no correlation matrix is calculated from the output signal based on the result of the saturation speculating process.

In FIG. 5, no arc-shaped artifact is observed. Further, in FIG. 5, the tissues in the body surface muscle layer and the parenchyma, which are visible in FIG. 4, have almost disappeared. However, in FIG. 5, the brightness levels on the lower side of the blood flow in the cross-section of the blood vessel in the middle left of the image have increased in a block-like formation.

To cope with this situation, as a second embodiment, an example will be explained in which an image is separated into two or more regions, so as to further apply an MTI filter by calculating a correlation matrix and an MTI filter for each of the sectional regions on the basis of an output signal based on a result of the saturation speculating process.

Figure 6:
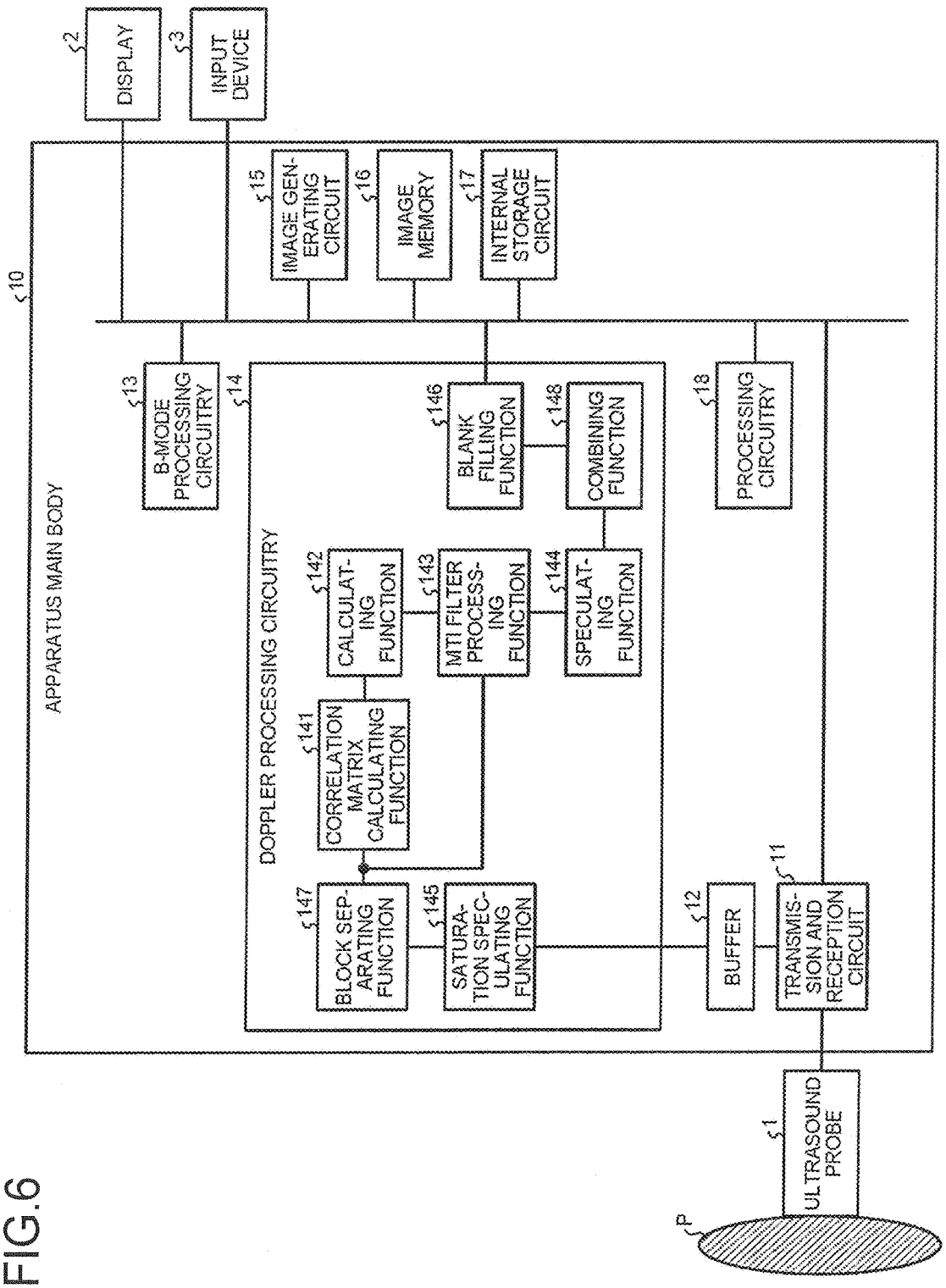
FIG. 6 is a block diagram illustrating an exemplary configuration of an ultrasound diagnosis apparatus according to a second embodiment.

FIG. 6 is a block diagram illustrating an exemplary configuration of the ultrasound diagnosis apparatus according to the second embodiment. The exemplary configuration of the ultrasound diagnosis apparatus according to the second embodiment illustrated in FIG. 6 is the same as the exemplary configuration of the ultrasound diagnosis apparatus according to the first embodiment illustrated in FIG. 1, except that the Doppler processing circuitry 14 further executes a block separating function 147 and a combining function 148. For this reason, in the second embodiment, only the block separating function 147 and the combining function 148 will be explained. The correlation matrix calculating function 141, the calculating function 142, the MTI filter processing function 143, the speculating function 144, the block separating function 147, and the combining function 148 according to the second embodiment are examples of an extracting unit.

Figure 7:
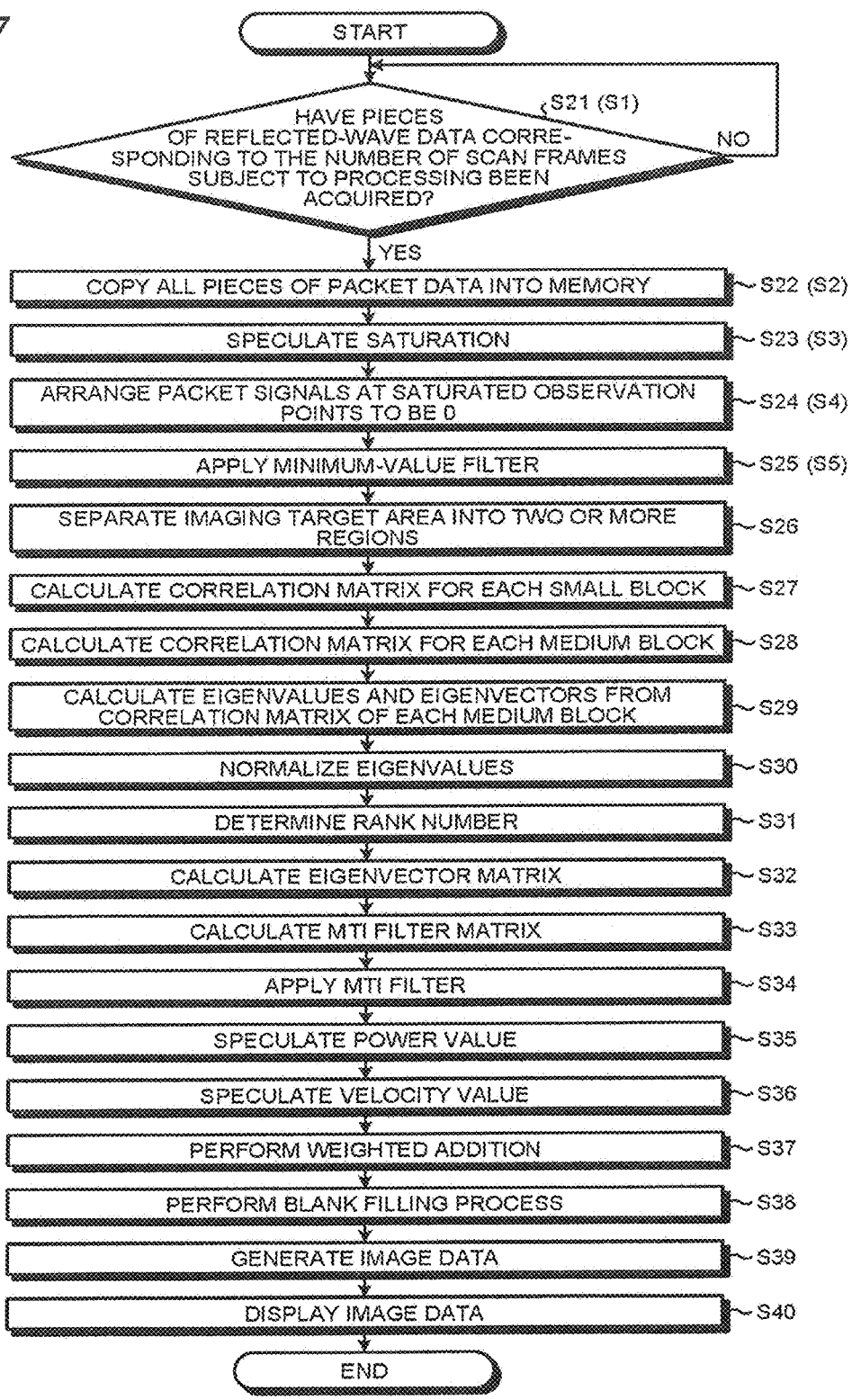
FIG. 7 is a flowchart illustrating a processing procedure performed by the ultrasound diagnosis apparatus according to the second embodiment.

FIG. 7 is a flowchart illustrating a processing procedure performed by the ultrasound diagnosis apparatus according to the second embodiment. With reference to FIG. 7, which step in the flowchart corresponds to each of the constituent elements of the ultrasound diagnosis apparatus will be explained. In the flowchart in FIG. 7, some of the processes that are the same as those in the flowchart in FIG. 3 will be referred to by using the same reference numbers, and detailed explanations thereof will be omitted.

Steps S21 through S25 are steps corresponding to the saturation speculating function 145. Steps S21 through S25 are steps at which the saturation speculating function 145 is realized as a result of the Doppler processing circuitry 14 invoking and executing a predetermined program corresponding to the saturation speculating function 145 from the internal storage circuit 17. The processes at steps S21 through S25 correspond to the processes at steps S1 through S5 illustrated in FIG. 3. In other words, the saturation speculating function 145 speculates saturation, outputs an output signal based on the result of the saturation speculating process, and applies a spatial minimum-value filter.

Figure 8:
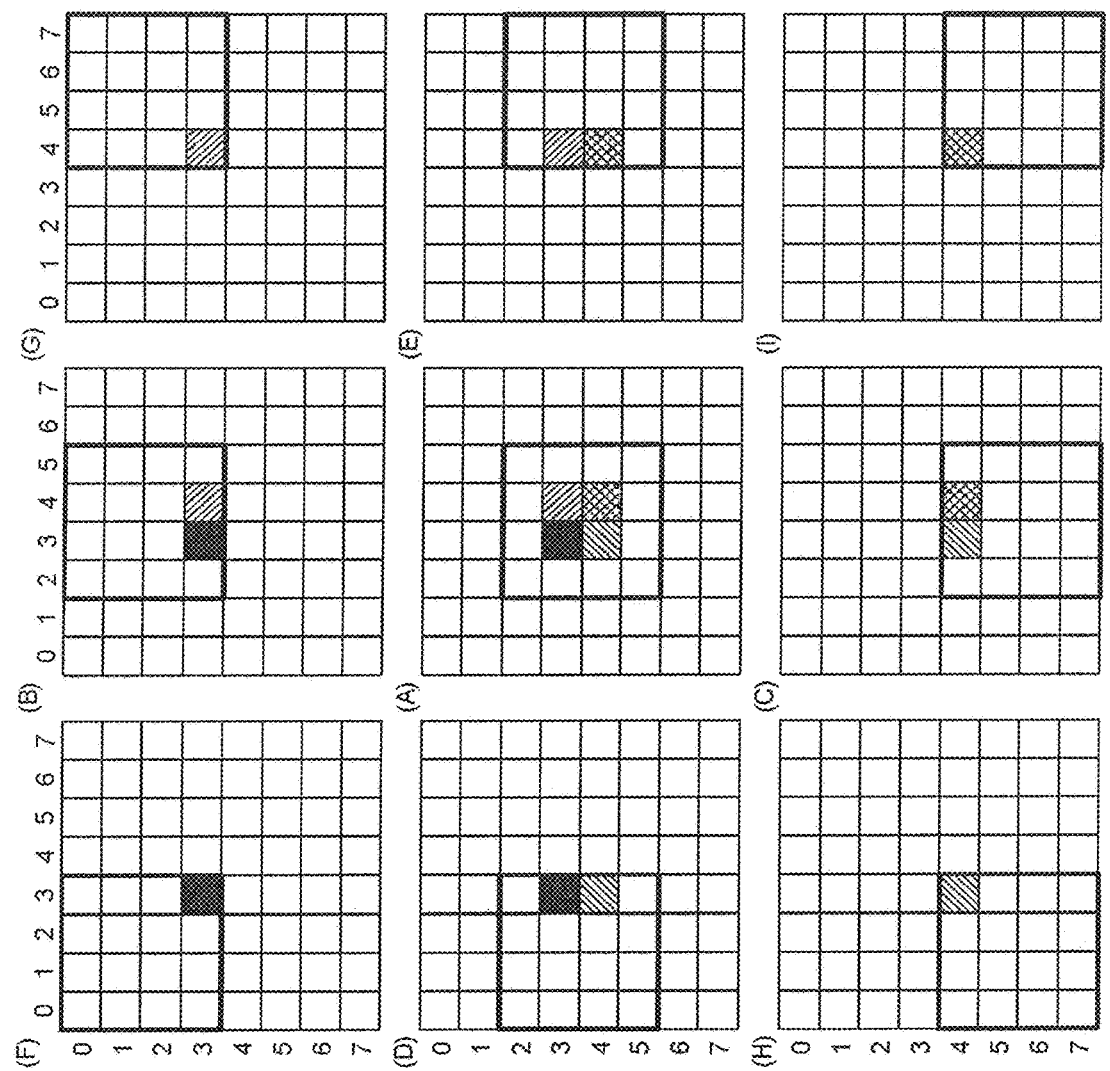
FIG. 8 is a drawing for explaining the second embodiment.

Step S26 is a step corresponding to the block separating function 147. Step S26 is a step at which the block separating function 147 is realized as a result of the Doppler processing circuitry 14 invoking and executing a predetermined program corresponding to the block separating function 147 from the internal storage circuit 17. At step S26, the block separating function 147 separates the imaging target area into two or more regions. FIG. 8 is a drawing for explaining the second embodiment. FIG. 8 illustrates a partial region of the entire imaging target area. Further, FIG. 8 illustrates examples of mutually the same region in which the region is separated by using nine separation patterns (A) to (I).

For example, the block separating function 147 separates the imaging target area into the two or more regions, by using the small squares in FIG. 8 as the smallest separation units. The smallest separation units will be referred to as small blocks. In patterns (A) to (I) in FIG. 8, the separation patterns of the small blocks are mutually the same. In one example, the block separating function 147 separates the area so that each of the small blocks contains four rasters and sixteen samples.

Further, the block separating function 147 forms medium blocks, by using two or more of the small blocks for each medium block. For example, the block separating function 147 forms each of the medium blocks by putting together sixteen small blocks, four across and four down, enclosed in the bold frame indicated in FIG. 8. In other words, each of the medium blocks is formed by 4×4 small blocks. In one example, the block separating function 147 forms each of the medium blocks as illustrated in patterns (A) to (I) in FIG. 8.

Next, an example will be explained by using the medium block enclosed in the bold frame in pattern (A) in FIG. 8. The medium block in (A) overlaps with the medium blocks in some of patterns (B) to (I) that are positioned adjacent to pattern (A). For example, the solid black small block in pattern (A) is also contained, in a duplicate manner, as a solid black small block in each of the medium blocks in patterns (B), (D), and (F). In this manner, all the locations are contained in four mutually-different medium blocks in a duplicate manner. In other words, the block separating function 147 separates the imaging target area into the regions, in such a manner that a part of each of the regions overlaps with a part of at least one of the other regions. That is to say, the block separating function 147 separates the scan range into the two or more regions, in such a manner that each of the sectional regions overlaps with at least one of the other sectional regions.

Steps S27 and S28 are steps corresponding to the correlation matrix calculating function 141. Steps S27 and S28 are steps at which the correlation matrix calculating function 141 is realized as a result of the Doppler processing circuitry 14 invoking and executing a predetermined program corresponding to the correlation matrix calculating function 141 from the internal storage circuit 17. At step S27, the correlation matrix calculating function 141 calculates a correlation matrix in each of the small blocks. In this situation, the correlation matrix calculating function 141 calculates the correlation matrix of each of the small blocks without performing the multiplication by 1/N indicated in Expression (3).

At step S28, the correlation matrix calculating function 141 calculates a correlation matrix of each of the medium blocks. For example, the correlation matrix calculating function 141 calculates the correlation matrix of each of the medium blocks formed by 4×4 small blocks. More specifically, the correlation matrix calculating function 141 calculates the correlation matrix of each of the medium blocks by adding together the correlation matrices calculated for the small blocks. In this situation, after calculating the correlation matrix of each of the medium blocks by adding together the correlation matrices calculated for the small blocks, the correlation matrix calculating function 141 divides the correlation matrix of each of the medium blocks by the total number N of pieces of spatial data in the medium block.

Steps S29 through S33 are steps corresponding to the calculating function 142. Steps S29 through S33 are steps at which the calculating function 142 is realized as a result of the Doppler processing circuitry 14 invoking and executing a predetermined program corresponding to the calculating function 142 from the internal storage circuit 17. At step S29, the calculating function 142 calculates eigenvalues and eigenvectors from the correlation matrix of each of the medium blocks. In this situation, the calculating function 142 calculates the eigenvalues and the eigenvectors from the correlation matrix of each of the medium blocks, in the same manner as at step S7 in FIG. 3.

At step S30, the calculating function 142 normalizes the eigenvalues. For example, the calculating function 142 calculates the correlation matrix of the entire image by adding together the correlation matrices calculated for the small blocks in the entire imaging target area. After that, in the same manner as at step S8 in FIG. 3, the calculating function 142 performs an eigenvalue decomposition for each of the medium blocks and subsequently normalizes the eigenvalues by using the largest eigenvalue of the correlation matrix of the entire image.

At step S31, the calculating function 142 calculates an optimal rank cut number k from the eigenvalues. For example, in the same manner as at step S9 in FIG. 3, the calculating function 142 may calculate the optimal rank cut number k for each of the medium blocks by using a method disclosed in Patent Literature 1 (Japanese Patent Laid-open No. 2014-158698) or as the smallest value that makes $\lambda_k$ equal to or smaller than a threshold value. By performing the normalizing process with the largest eigenvalue in the correlation matrix of the entire image in this manner, it is possible to eliminate gain dependency and impacts of differences among tissues in the patient's body caused by the region separating process.

At step S32, the calculating function 142 calculates an eigenvalue matrix in the same manner as at step S10 in FIG. 3. At step S33, in the same manner as at step S11 in FIG. 3, the calculating function 142 calculates an MTI filter matrix. In other words, the calculating function 142 normalizes the eigenvalues of the correlation matrices of the sectional regions obtained by separating the image, while using the largest eigenvalue of the correlation matrix of the entire image and further calculates a filter coefficient by determining a rank cut number by using the normalized eigenvalues.

Step S34 is a step corresponding to the MTI filter processing function 143. Step S34 is a step at which the MTI filter processing function 143 is realized as a result of the Doppler processing circuitry 14 invoking and executing a predetermined program corresponding to the MTI filter processing function 143 from the internal storage circuit 17. At step S34, to the data of each of the medium blocks, the MTI filter processing function 143 applies an MTI filter calculated from the medium block.

For example, the MTI filter processing function 143 applies an MTI filter calculated from the data of a medium block in (A) formed by 4×4 small blocks, to the data of the medium block in (A) formed by the 4×4 small blocks. In this situation, to the data of each of the medium blocks processed by the saturation speculating function 145, the MTI filter processing function 143 applies the MTI filter calculated from the medium block. Alternatively, to the data of each of the medium blocks that has not been processed by the saturation speculating function 145, the MTI filter processing function 143 may apply an MTI filter calculated from the medium block.

Steps S35 and S36 are steps corresponding to the speculating function 144. Steps S35 and S36 are steps at which the speculating function 144 is realized as a result of the Doppler processing circuitry 14 invoking and executing a predetermined program corresponding to the speculating function 144 from the internal storage circuit 17. At steps S35 and S36, the speculating function 144 extracts the moving member information of each of the sectional regions by using a statistical characteristic calculated from the sectional region, the sectional regions having been obtained by separating the scan range formed with the plurality of scanning lines into two or more regions. In this situation, the speculating function 144 separates the scan range into the two or more regions, in such a manner that each of the sectional regions overlaps with at least one of the other sectional regions and further extracts the moving member information by calculating a statistical characteristic of the region where two or more of the sectional regions overlap with one another while using the statistical characteristics of the sectional regions.

More specifically, at step S35, the speculating function 144 speculates a power value P in the same manner as at step S13, by using the data of the medium blocks to which the MTI filter was applied at step S34. Further, at step S36, the speculating function 144 speculates a velocity value V in the same manner as at step S14, by using the data of the medium blocks to which the MTI filter was applied at step S34.

Figure 9:
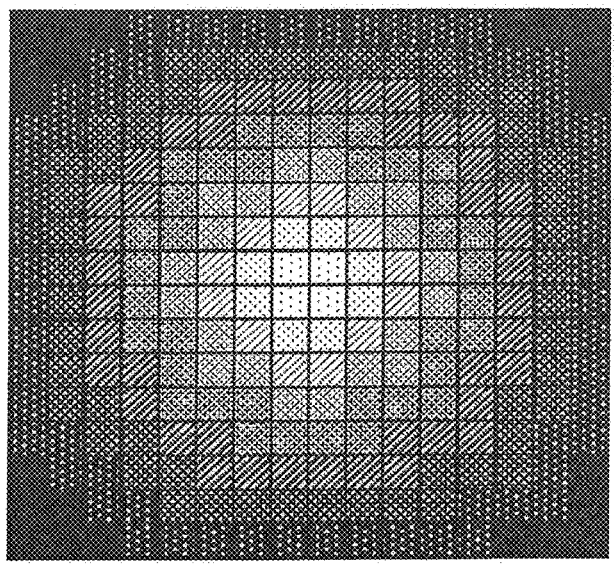
FIG. 9 is another drawing for explaining the second embodiment.

Step S37 is a step corresponding to the combining function 148. Step S37 is a step at which the combining function 148 is realized as a result of the Doppler processing circuitry 14 invoking and executing a predetermined program corresponding to the combining function 148 from the internal storage circuit 17. At step S37, the combining function 148 performs a weighted addition process. FIG. 9 is another drawing for explaining the second embodiment. FIG. 9 illustrates a distribution of weights corresponding to different positions. For example, the combining function 148 interpolates pixels by performing multiplication with weight coefficients corresponding to the different positions while implementing a bi-linear method that uses the weight coefficients illustrated in FIG. 8 and performing addition using the data in the same position.

Step S38 is a step corresponding to the blank filling function 146. Step S38 is a step at which the blank filling function 146 is realized as a result of the Doppler processing circuitry 14 invoking and executing a predetermined program corresponding to the blank filling function 146 from the internal storage circuit 17. At step S38, the blank filling function 146 performs the blank filling process in the same manner as at step S15.

Step S39 is a step realized by the image generating circuit 15. At step S39, the image generating circuit 15 generates color Doppler image data from the moving member information in the same manner as at step S16. In this situation, for example, the image generating circuit 15 generates the image data based on the moving member information of the sectional regions. Step S40 is a step realized by the processing circuitry 18. At step S40, the processing circuitry 18 causes the display 2 to display the color Doppler image data in the same manner as at step S17.

Figure 10:
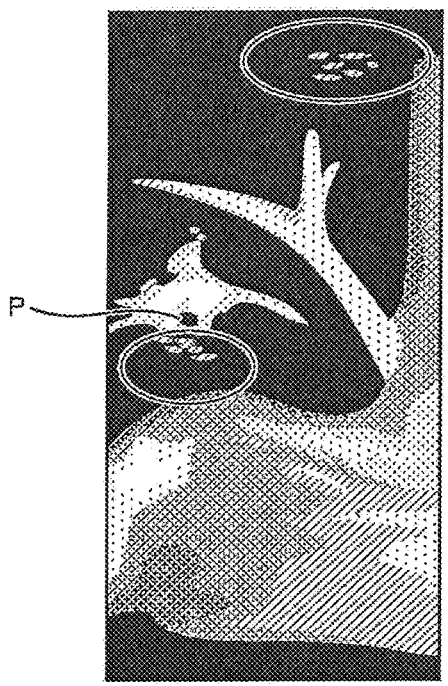
FIG. 10 is yet another drawing for explaining the second embodiment.

FIG. 10 is yet another drawing for explaining the second embodiment. FIG. 10 illustrates an example in which the power values of a blood flow are rendered in an image, by performing a weighted addition process while performing the saturation process in the same manner as illustrated in FIG. 4 for each of the blocks. As illustrated in FIG. 10, the blood vessel wall on the cross-section of the blood vessel in the middle left of the image is saturated and looks dark and missing. In comparison to FIG. 5, the tissues in the body surface muscle layer have almost disappeared in FIG. 10. Further, the increase in the brightness levels on the lower side of the blood flow in the cross-section of the blood vessel in the middle left of the image is also suppressed, as compared to the example in FIG. 5.

As explained above, the ultrasound diagnosis apparatus according to the second embodiment is configured to speculate the saturation at each of the observation points in accordance with the intensity of the reflected-wave data generated through the phased addition process and to further calculate the correlation matrix of each of the sectional regions by using the output result in which the signals of the observation points speculated to have saturation are suppressed. With this arrangement, according to the second embodiment, it is possible to reduce the impacts of the saturated signals imposed on the correlation matrices. As a result, according to the second embodiment, it is possible to improve the image quality while implementing the CFM method.

Further, in the second embodiment, the block separating function 147 is configured to separate the imaging target area into the small blocks as illustrated in FIG. 8. Accordingly, the correlation matrix calculating function 141 is able to calculate the correlation matrix of each of the medium blocks, by adding together the correlation matrices of the small blocks. Further, because the medium blocks overlap with one another in units of small blocks, there is no waste in the calculations of the correlation matrices. Furthermore, by arranging the spatial data and the packet data to be stored in a memory in units of small blocks, it is possible to achieve excellent cache efficiency when a CPU executes the MTI filter matrix calculations.

According to the second embodiment described above, the example is explained in which the block separating function 147 is configured to form the medium blocks in such a manner that a part of each of the medium blocks overlaps with a part of at least one of the other medium blocks; however, possible embodiments are not limited to this example. For instance, the block separating function 147 may form the medium blocks in such a manner that a part of each of the medium blocks does not overlap with a part of any other medium block.

Third Embodiment

In a third embodiment, an example will be explained in which, by using a power signal $P_1$ generated in the first embodiment and another power signal $P_2$ generated in the second embodiment, a final output power signal $P_3$ is determined.

An exemplary configuration of the ultrasound diagnosis apparatus according to the third embodiment is the same as the exemplary configuration of the ultrasound diagnosis apparatus according to the second embodiment illustrated in FIG. 6, except that the speculating function 144 and the image generating circuit 15 are additionally provided with certain functions. For this reason, in the third embodiment, only the speculating function 144 and the image generating circuit 15 will be explained.

Figure 11A:
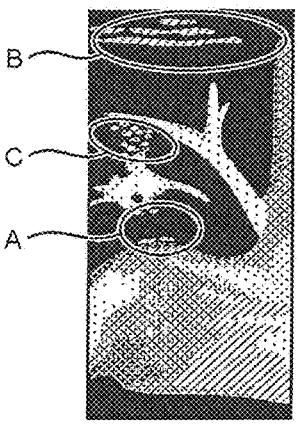
FIG. 11A is a drawing for explaining a third embodiment.
Figure 11B:
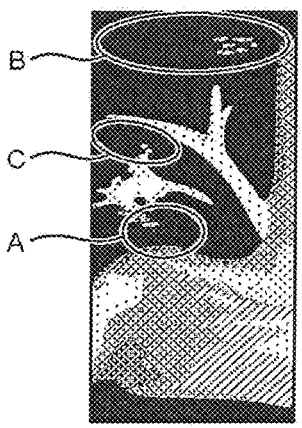
FIG. 11B is another drawing for explaining the third embodiment.
Figure 11C:
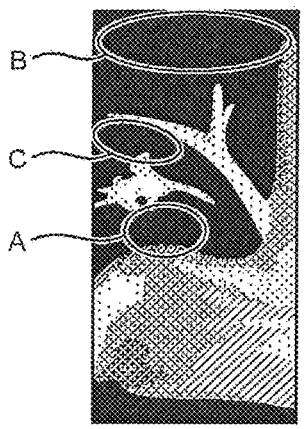
FIG. 11C is yet another drawing for explaining the third embodiment.

The speculating function 144 according to the third embodiment is configured to extract first moving member information by using a statistical characteristic calculated from the scan range formed with the plurality of scanning lines and is configured to further extract second moving member information of each of the sectional regions, by using a statistical characteristic calculated from the sectional region, the sectional regions having been obtained by separating the scan range into two or more regions. In this situation, the speculating function 144 according to the third embodiment calculates power values as the first moving member information and the second moving member information. FIGS. 11A to 11C are drawings for explaining the third embodiment. FIG. 11A illustrates an example of image data based on the first moving member information. FIG. 11B illustrates an example of image data based on the second moving member information.

For example, in FIGS. 11A and 11B, as regions B and C that are circled are compared between the drawings, tissue suppressing capability is higher in FIG. 11B. Further, in FIG. 11B, an increase is exhibited in the brightness levels on the lower side of the blood flow in the cross-section of the blood vessel in the middle left of the image (region A being circled); in contrast, no such increase is exhibited in FIG. 11A. It is considered that the increase in the brightness levels is caused because the blood vessel wall is saturated, and there are other sites that are saturated in the CH signals observed before the beam forming process, in addition to the site that is detected to have saturation. There is a possibility that the correlation matrix may be under a bad influence of the undetected saturated signals and that the MTI filter matrix may have not been correctly calculated.

In contrast, in the example in FIG. 11A, because the correlation matrix is calculated from the entire image, the weights of local undetected saturated signals are smaller. Further, in FIG. 11B, the brightness levels of the edges of the large blood vessel is slightly higher; in contrast, in FIG. 11A, because the brightness levels of the tissue at the edge of the large blood vessel have become lower, the contrast is improved. The reason is that, when the large blood vessel is contained in a majority part of a sectional region, more signal components of the blood vessel are present in the correlation matrix, and therefore, the tissues are no longer the only principal components.

As explained above, the two images in FIGS. 11A and 11B have advantages and disadvantages. For this reason, the image generating circuit 15 according to the third embodiment puts together the advantages of the two images. In other words, the image generating circuit 15 according to the third embodiment generates image data based on the first moving member information and the second moving member information. For example, the image generating circuit 15 according to the third embodiment calculates a final output power signal $P_3$ by using Expression (20) presented below.

$$P_3 = \min(\alpha P_1, P_2) \quad (20)$$

In other words, the image generating circuit 15 according to the third embodiment is configured to determine the smaller between a signal obtained by multiplying $P_1$ by a coefficient $\alpha$ and $P_2$, to be the final output power signal $P_3$. In other words, the image generating circuit 15 according to the third embodiment generates first image data based on the power value calculated as the first moving member information and second image data based on the power value calculated as the second moving member information. Subsequently, the image generating circuit 15 according to the third embodiment generates image data by multiplying the power value of at least one selected from between the first image data and the second image data by the coefficient and further selecting the smaller value between the power value of the first image data and the power value of the second image data. In Expression (20), $\alpha=0.75$ is satisfied. The value of $\alpha$ is a value determined in advance and may arbitrarily be set. FIG. 11C illustrates an example of image data based on the final output power signal $P_3$. Unlike the example in FIG. 11B, no increase is exhibited in FIG. 11C in the brightness levels on the lower side of the blood flow in the cross-section of the blood vessel in the middle left of the image (region A being circled), and the contrast at the edge of the blood vessel is improved.

As explained above, according to the third embodiment, the image data based on the first moving member information and the second moving member information is generated. As a result, according to the third embodiment, it is possible to improve the image quality while implementing the CFM method.

Fourth Embodiment

Even when the power signal selecting process explained in the third embodiment above is performed, gain differences among the blocks may be conspicuous in some situations. For example, it is considered that the cause may be the occurrence of a side lobe caused by saturation in the vicinity of a powerful reflecting member or because the intensities of reflected echo from the tissues are different among the blocks. To cope with this situation, as a fourth embodiment, an example will be explained in which, for the purpose of suppressing the gain differences among the blocks, a gain correction is performed for each of the blocks.

Figure 12:
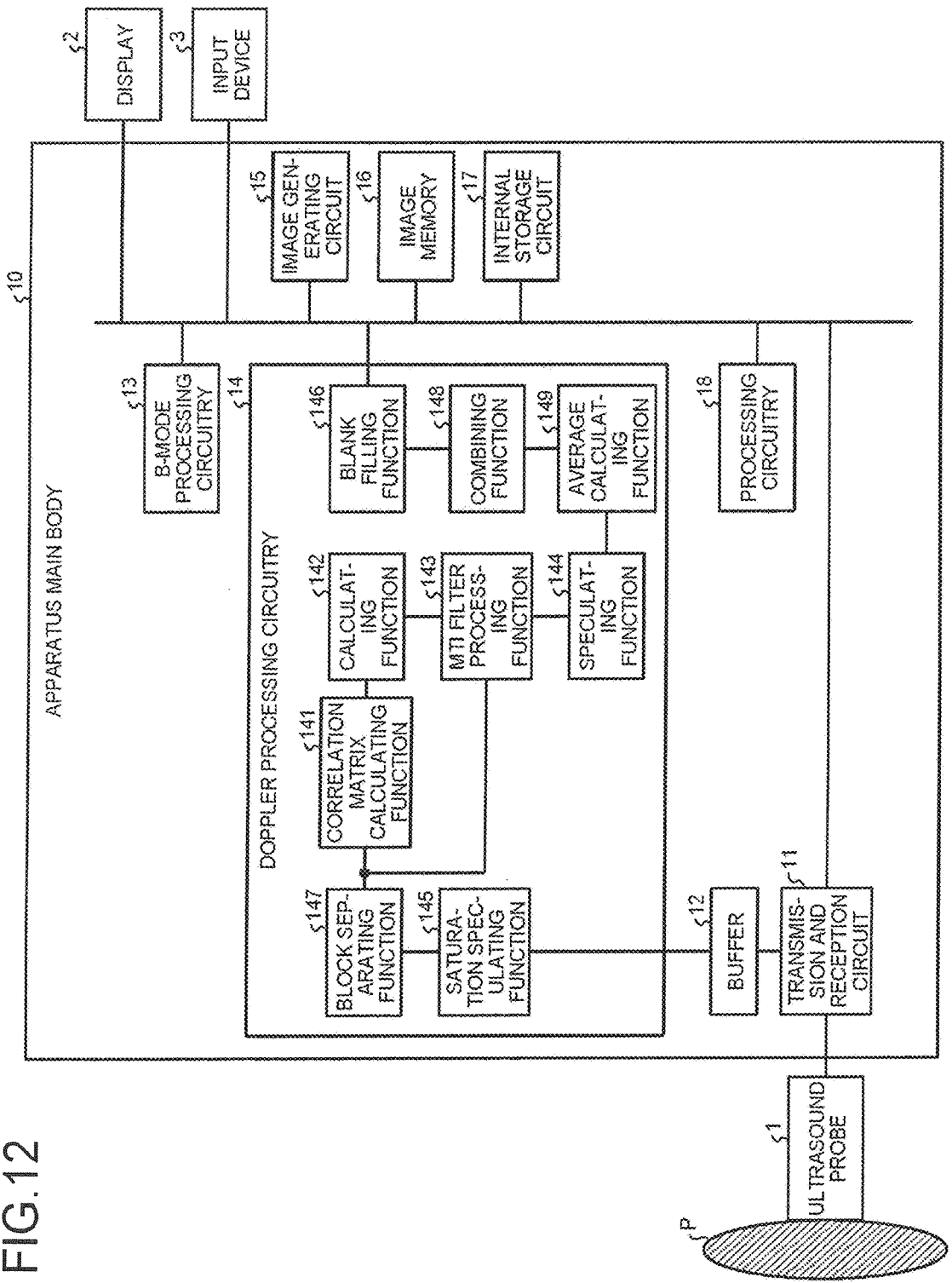
FIG. 12 is a block diagram illustrating an exemplary configuration of an ultrasound diagnosis apparatus according to a fourth embodiment.

FIG. 12 is a block diagram illustrating an exemplary configuration of an ultrasound diagnosis apparatus according to the fourth embodiment. The exemplary configuration of the ultrasound diagnosis apparatus according to the fourth embodiment illustrated in FIG. 12 is the same as the exemplary configuration of the ultrasound diagnosis apparatus according to the second embodiment illustrated in FIG. 6, except that the Doppler processing circuitry 14 further executes an average calculating function 149 and that a part of the functions of the combining function 148 is different. For this reason, in the fourth embodiment, only the average calculating function 149 and the combining function 148 will be explained.

For example, the average calculating function 149 is configured to calculate an average value of moving member information of each of the sectional regions. The combining function 148 is configured to correct the pieces of moving member information of the sectional regions by using the average values. The correlation matrix calculating function 141, the calculating function 142, the MTI filter processing function 143, the speculating function 144, the average calculating function 149, and the combining function 148 according to the fourth embodiment are examples of an extracting unit.

Figure 13:
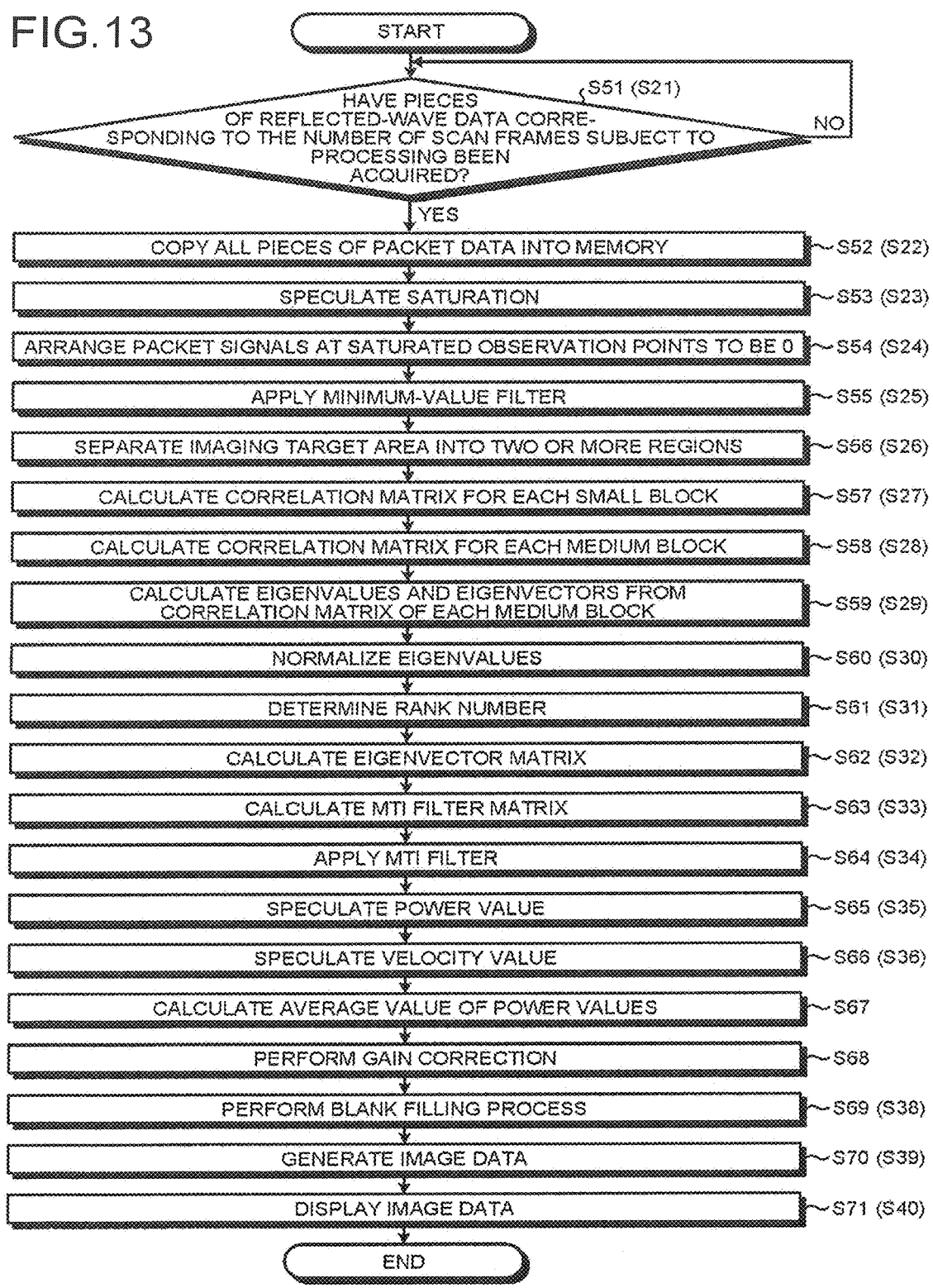
FIG. 13 is a flowchart illustrating a processing procedure performed by the ultrasound diagnosis apparatus according to the fourth embodiment.

FIG. 13 is a flowchart illustrating a processing procedure performed by the ultrasound diagnosis apparatus according to the fourth embodiment. With reference to FIG. 13, which step in the flowchart corresponds to each of the constituent elements of the ultrasound diagnosis apparatus will be explained. In the flowchart in FIG. 13, some of the processes that are the same as those in the flowchart in FIG. 7 will be referred to by using the same reference numbers, and detailed explanations thereof will be omitted. For example, the processes at steps S51 through S66 illustrated in FIG. 13 correspond to the processes at steps S21 through S36 illustrated in FIG. 7.

Steps S67 is a step corresponding to the average calculating function 149. Steps S67 is a step at which the average calculating function 149 is realized as a result of the Doppler processing circuitry 14 invoking and executing a predetermined program corresponding to the average calculating function 149 from the internal storage circuit 17. At step S67, the average calculating function 149 calculates an average of power values for each of the medium blocks.

Step S68 is a step corresponding to the combining function 148. Step S68 is a step at which the combining function 148 is realized as a result of the Doppler processing circuitry 14 invoking and executing a predetermined program corresponding to the combining function 148 from the internal storage circuit 17. At step S68, the combining function 148 performs a gain correction. In this situation, for example, the power value at each of the points in the block will be expressed as $P_i$, while an average value will be expressed as $P_0$, and either an average value or the smallest value of eight adjacently-positioned blocks excluding the block in question will be expressed as $P_1$. In that situation, the combining function 148 corrects the power values by using Expression (21) presented below while using $T_h$ as a threshold value. In other words, the combining function 148 corrects the pieces of moving member information of the sectional regions in such a manner that the average values are each equal to an average value of the adjacently-positioned sectional regions.

$$P_i = \begin{cases} \frac{T_h P_1}{P_0} P_i & \text{if } \left(\frac{P_0}{P_1} > T_h\right) \\ P_i & \text{otherwise} \end{cases} \quad (21)$$

In this situation, when an increase in the brightness levels is exhibited over a large area or the like, it may be desirable in some situations for the combining function 148 to use the smallest value as the value of $P_1$, instead of the average value of the neighboring blocks.

Processes at steps S69 through S71 illustrated in FIG. 13 correspond to the processes at steps S38 through S40 illustrated in FIG. 7. Accordingly, the image generating circuit 15 generates image data based on the corrected pieces of moving member information of the sectional regions.

As explained above, according to the fourth embodiment, the gain correction is performed for each of the blocks, by calculating the average value of moving member information of each of the sectional regions, correcting the pieces of moving member information of the sectional regions by using the average values, and generating the image data based on the corrected pieces of moving member information of the sectional regions. With these arrangements, according to the fourth embodiment, it is possible to improve the image quality while implementing the CFM method.

A Modification Example of Fourth Embodiment

In the fourth embodiment described above, the example is explained in which the gain correction is performed after the signal saturation speculating process is performed; however, possible embodiments are not limited to this example. For instance, when the gain correction is to be performed, the signal saturation speculating process does not necessarily have to be performed.

Figure 14:
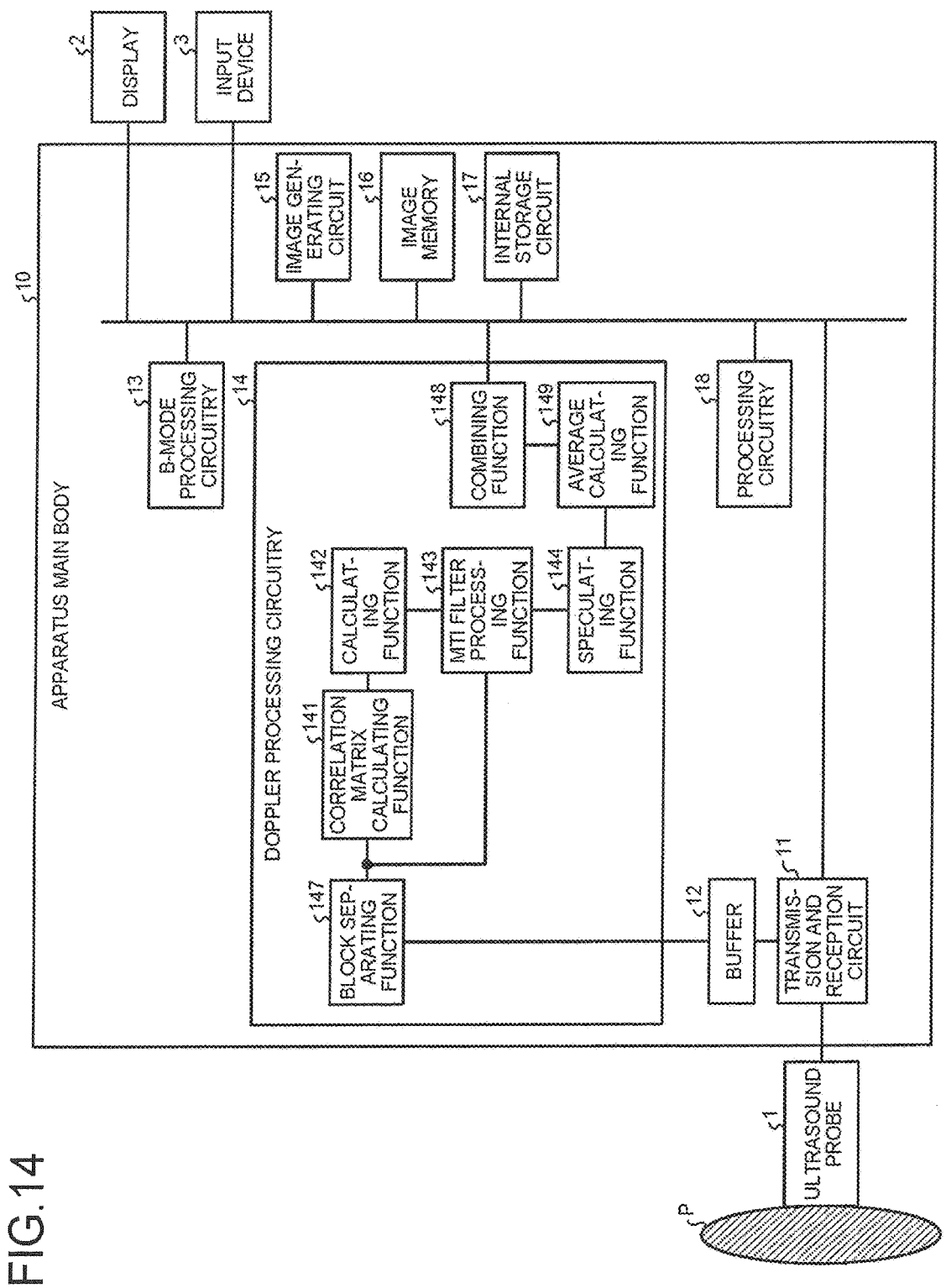
FIG. 14 is a block diagram illustrating an exemplary configuration of an ultrasound diagnosis apparatus according to a modification example of the fourth embodiment.

FIG. 14 is a block diagram illustrating an exemplary configuration of an ultrasound diagnosis apparatus according to a modification example of the fourth embodiment. The exemplary configuration of the ultrasound diagnosis apparatus according to the modification example of the fourth embodiment illustrated in FIG. 14 is the same as the exemplary configuration of the ultrasound diagnosis apparatus according to the fourth embodiment illustrated in FIG. 12, except that the exemplary configuration of the Doppler processing circuitry 14 is different. For this reason, in the modification example of the fourth embodiment, only the Doppler processing circuitry 14 will be explained.

As illustrated in FIG. 14, the Doppler processing circuitry 14 according to the modification example of the fourth embodiment executes the correlation matrix calculating function 141, the calculating function 142, the MTI filter processing function 143, the speculating function 144, the block separating function 147, the combining function 148, and the average calculating function 149.

The block separating function 147 is configured to separate the imaging target area into two or more regions. The correlation matrix calculating function 141 is configured to calculate a correlation matrix in each of the small blocks. Further, the correlation matrix calculating function 141 is configured to calculate a correlation matrix of each of the medium blocks. The calculating function 142 is configured to calculate eigenvalues and eigenvectors from the correlation matrices of the medium blocks and to calculate an MTI filter matrix. The MTI filter processing function 143 is configured to apply the MTI filter calculated from each of the medium blocks to the medium block.

The speculating function 144 is configured to extract moving member information from the data of each of the medium blocks to which the MTI filter has been applied. In other words, the speculating function 144 is configured to extract the moving member information of each of the sectional regions by using a statistical characteristic calculated from the sectional region, by using a data sequence represented by a set made up of pieces of reflected-wave data generated through a phased addition process performed on the reflected-wave signals generated by transmitting an ultrasound wave with respect to mutually the same scanning line, the sectional regions having been obtained by separating a scan range formed with a plurality of scanning lines into two or more regions. The average calculating function 149 is configured to calculate an average value of moving member information of each of the sectional regions. The combining function 148 is configured to correct the pieces of moving member information of the sectional regions by using the average values. Further, the image generating circuit 15 is configured to generate image data based on the corrected pieces of moving member information of the sectional regions.

As explained above, according to the modification example of the fourth embodiment, the gain correction is performed for each of the blocks, by calculating the average value of moving member information of each of the sectional regions, correcting the pieces of moving member information of the sectional regions by using the average values, and generating the image data based on the corrected pieces of moving member information of the sectional regions. With these arrangements, according to the modification example of the fourth embodiment, it is possible to improve the image quality while implementing the CFM method.

Fifth Embodiment

In the embodiments described above, the example is explained in which, when the CFM method is implemented, as the data based on the result of the signal saturation speculating process, the blood flow image in which the impacts of the saturated signals are alleviated is generated; however, possible embodiments are not limited to the example in which the blood flow image is generated. For example, the ultrasound diagnosis apparatus may be configured to generate evaluation-purpose image data, as data based on the result of the signal saturation speculating process.

Figure 15:
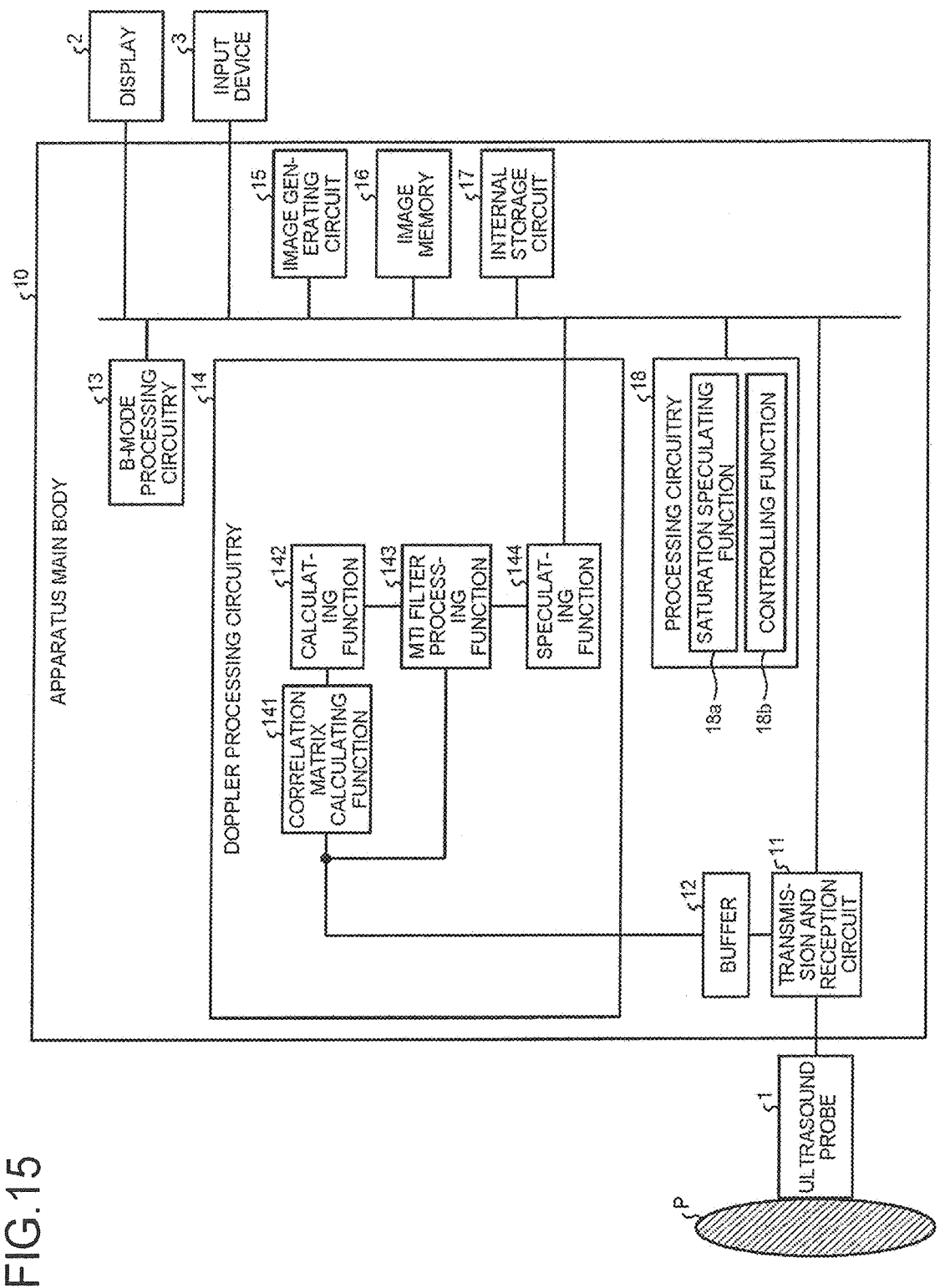
FIG. 15 is a block diagram illustrating an exemplary configuration of an ultrasound diagnosis apparatus according a fifth embodiment.

FIG. 15 is a block diagram illustrating an exemplary configuration of an ultrasound diagnosis apparatus according to a fifth embodiment. An exemplary configuration of the ultrasound diagnosis apparatus according to the fifth embodiment illustrated in FIG. 15 is the same as the exemplary configuration of the ultrasound diagnosis apparatus according to the first embodiment illustrated in FIG. 1, except that the configurations of the Doppler processing circuitry 14 and the processing circuitry 18 are different. For this reason, in the fifth embodiment, only the Doppler processing circuitry 14 and the processing circuitry 18 will be explained.

The Doppler processing circuitry 14 according to the fifth embodiment executes the correlation matrix calculating function 141, the calculating function 142, the MTI filter processing function 143, and the speculating function 144. In this situation, for example, the processing functions executed by the constituent elements of the Doppler processing circuitry 14 illustrated in FIG. 15, namely, the correlation matrix calculating function 141, the calculating function 142, the MTI filter processing function 143, and the speculating function 144, are each recorded in the internal storage circuit 17 in the form of a computer-executable program. For example, the Doppler processing circuitry 14 is a processor and is configured to read the programs from the internal storage circuit 17 and to realize the functions corresponding to the read programs by executing the read programs. In other words, the Doppler processing circuitry 14 that has read the programs has the functions illustrated within the Doppler processing circuitry 14 in FIG. 15.

The processing circuitry 18 according to the fifth embodiment executes a saturation speculating function 18a and a controlling function 18b. In this situation, for example, the processing functions executed by the constituent elements of the processing circuitry 18 illustrated in FIG. 15, namely, the saturation speculating function 18a and the controlling function 18b, are each recorded in the internal storage circuit 17 in the form of a computer-executable program. For example, the processing circuitry 18 is a processor and is configured to read the programs from the internal storage circuit 17 and to realize the functions corresponding to the read programs by executing the read programs. In other words, the processing circuitry 18 that has read the programs has the functions illustrated within the processing circuitry 18 in FIG. 15.

For example, the saturation speculating function 18a is configured to speculate saturation of the reflected-wave signals observed before the phased addition process performed by using the reflected-wave signals, in accordance with the intensity of the reflected-wave data generated through the phased addition process, the reflected-wave signals being generated by transmitting an ultrasound wave with respect to mutually the same scanning line, and the saturation speculating function 18a is configured to further output a result of the speculation. In this situation, the saturation speculating function 18a is an example of a saturation speculating unit.

The controlling function 18b is configured to cause the display 2 to display data based on the result of the speculation. In this situation, the controlling function 18b is an example of a controlling unit.

Figure 16:
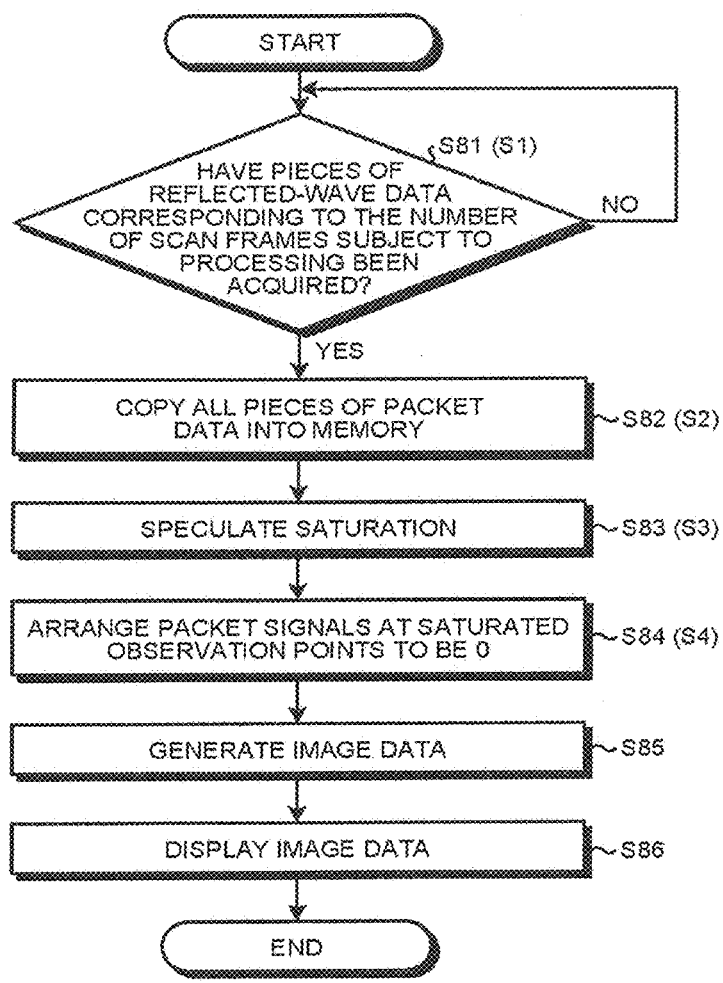
FIG. 16 is a flowchart illustrating a processing procedure performed by the ultrasound diagnosis apparatus according to the fifth embodiment.

FIG. 16 is a flowchart illustrating a processing procedure performed by the ultrasound diagnosis apparatus according to the fifth embodiment. With reference to FIG. 16, which step in the flowchart corresponds to each of the constituent elements of the ultrasound diagnosis apparatus will be explained. In the flowchart in FIG. 16, some of the processes that are the same as those in the flowchart in FIG. 3 will be referred to by using the same reference numbers, and detailed explanations thereof will be omitted.

Further, it is also acceptable to perform the processes illustrated in FIG. 16 prior to the implementation of the CFM method, to perform the processes by using the data at the time of implementation of the CFM method, or to perform the processes together with implementation of the CFM method in a time-division manner. It is assumed that the scan range in the processes illustrated in FIG. 16 contains at least a part of the scan range on which the CFM method is implemented. Further, in the fifth embodiment, when the CFM method is implemented, it is acceptable to use either a filter having a fixed coefficient or an adaptive MTI filter, as the MTI filter.

Processes at steps S81 through S85 illustrated in FIG. 16 are steps realized by the saturation speculating function 18a. Steps S81 through S85 are steps at which the saturation speculating function 18a is realized as a result of the processing circuitry 18 invoking and executing a predetermined program corresponding to the saturation speculating function 18a from the internal storage circuit 17. At steps S81 through S84, in the same manner with the processes at steps S1 through S4 illustrated in FIG. 3, the saturation speculating function 18a speculates saturation of the reflected-wave signals observed before the phased addition process performed by using the reflected-wave signals, in accordance with the intensity of the reflected-wave data generated through the phased addition process, the reflected-wave signals being generated by transmitting an ultrasound wave with respect to mutually the same scanning line, and the saturation speculating function 18a further outputs a result of the speculation. The saturation speculating function 18a uses 0 as an output value for each of the observation points at which the reflected-wave signal is saturated and uses the intensity of the reflected-wave data as an output value for each of the observation points at which the reflected-wave signal is not saturated.

Figure 17:
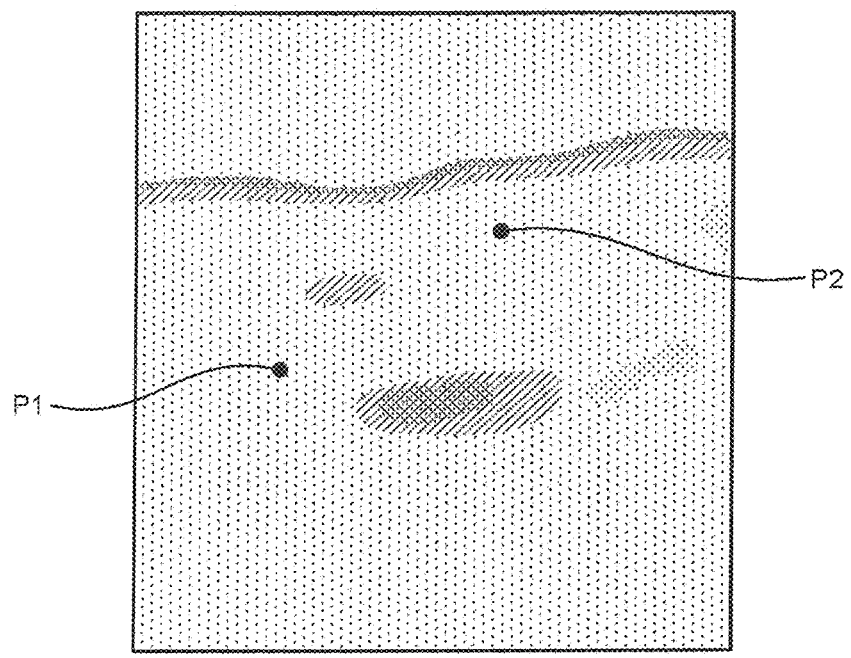
FIG. 17 is a drawing for explaining the fifth embodiment.

At step S85, the saturation speculating function 18a generates evaluation-purpose image data. For example, the saturation speculating function 18a generates the output values corresponding to the observation points obtained by the saturation speculating function 18a as the evaluation-purpose image data. FIG. 17 is a drawing for explaining the fifth embodiment. For example, as illustrated in FIG. 17, the saturation speculating function 18a generates the evaluation-purpose image data in which the output values are kept in correspondence with the observation points. In this situation, in FIG. 17, the observation points at which the reflection signals are saturated are indicated with solid black areas P1 and P2.

The process at step S86 is a step realized by the controlling function 18b. Step S86 is a step at which the controlling function 18b is realized as a result of the processing circuitry 18 invoking and executing a predetermined program corresponding to the controlling function 18b from the internal storage circuit 17. At step S86, the controlling function 18b causes the display 2 to display the evaluation-purpose image data. As a result, an operator of the ultrasound diagnosis apparatus is able to check to see whether or not there is an observation point at which the reflected-wave signal is saturated in the ultrasound scan range. For example, when there is no observation point at which the reflected-wave signal is saturated, the operator is able to evaluate that the measured values obtained from the ultrasound scan are not impacted by saturation and therefore have high reliability. On the contrary, when there are one or more observation points at which the reflected-wave signals are saturated, the operator is able to evaluate that the measured values obtained from the ultrasound scan are impacted by the saturation and therefore have low reliability. In addition to using the reliability of the measured values for the assessment as to whether the image is correct or not, it is also possible to use the evaluation as an index for reliability of measured values to determine whether the measured values obtained by counting the number of pixels in a region where a blood flow is present to assess whether the blood flow is abundant or scarce are reliable or not.

As explained above, in the fifth embodiment, the output values corresponding to the observation points are generated as the evaluation-purpose image data and are displayed on the display 2. Accordingly, it is possible to evaluate the reliability of the measured values. As a result, according to the fifth embodiment, it is possible to improve the image quality while implementing the CFM method.

Further, in the embodiment described above, the example is explained in which the saturation speculating function 18a generates the evaluation-purpose image data in which the output values are kept in correspondence with the observation points; however possible embodiments are not limited to this example. For instance, the saturation speculating function 18a may generate text information and/or audio information indicating the degrees of saturation at the observation points, as the data based on the result of the speculation.

Other Embodiments

Possible embodiments are not limited to the embodiments described above.

In the embodiments described above, the example is explained in which, when at least one of the packets in mutually the same location point exhibits saturated signals, the saturation speculating function 145 arranges all the packet signals to be 0 as a result of the speculation; however, possible embodiments are not limited to this example. For instance, the saturation speculating function 145 may be configured to output an output signal obtained by multiplying the reflected-wave data by a predetermined coefficient of which the value is smaller than 1, when having speculated that the reflected-wave signals observed before the phased addition process are saturated.

The term "processor" used in the explanation above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). Each of the processors realizes the functions thereof by reading and executing a corresponding one of the programs stored in a storage circuit. In this situation, instead of saving the programs in the storage circuit, it is also acceptable to directly incorporate the programs in the circuits of the processors. In that situation, each of the processors realizes the functions thereof by reading and executing the corresponding one of the programs incorporated in the circuit thereof. Further, the processors in the present embodiments do not each necessarily have to be structured as a single circuit. It is also acceptable to structure one processor by combining together a plurality of independent circuits so as to realize the functions thereof. Further, it is also acceptable to integrate two or more of constituent elements illustrated in FIG. 1 into a single processor so as to realize the functions thereof.

The constituent elements of the apparatuses and the devices illustrated in the drawings used in the explanations of the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the medical image processing methods explained in the above embodiments may be realized by causing a computer such as a personal computer or a workstation to execute a control program prepared in advance. The control program may be distributed via a network such as the Internet. Further, the control program may be recorded on a computer-readable recording medium such as a hard disk, a flexible disk (FD), Compact Disk Read-Only Memory (CD-ROM), a Magneto-Optical (MO) disk, or a Digital Versatile Disk (DVD), so as to be executed as being read from the recording medium by a computer.

According to at least one aspect of the embodiments described above, it is possible to improve the image quality while implementing the CFM method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
processing circuitry configured to
calculate, in accordance with an intensity of digital reflected-wave data generated through a phased addition process, a saturation value for analog reflected-wave signals observed before the phased addition process is performed, the analog reflected-wave signals being generated by transmitting an ultrasound wave with respect to a mutually same scanning line, and the digital reflected-wave data being digital signals being generated by performing an analog to digital conversion on the analog reflected-wave signals;
produce processed reflected-wave data by: (1) when the calculated saturation value is at least a threshold value indicating saturation, outputting as corresponding processed reflected-wave data, data obtained by multiplying the digital reflected-wave data by a predetermined coefficient having a non-zero value smaller than 1, and (2) when the calculated saturation value is less than the threshold value indicating saturation, outputting as corresponding processed reflected-wave data, the digital reflected-wave data; and
cause a display to display data based on the processed reflected-wave data.

2. The ultrasound diagnosis apparatus according to claim 1, wherein the processing circuitry is further configured to:
extract moving member information based on the calculated saturation value,
generate first image data based on the moving member information, and
cause the display to display the first image data based on the moving member information.

3. The ultrasound diagnosis apparatus according to claim 2, wherein the processing circuitry is further configured to:
generate saturation values and produce processed reflected-wave data for a plurality of frames; and
extract the moving member information by using a statistical characteristic based on the saturation values for the plurality of frames.

4. The ultrasound diagnosis apparatus according to claim 3, wherein the processing circuitry is further configured to, when a respective saturation value of the saturation values for the plurality of frames indicates saturation, exclude the corresponding processed reflected-wave data when extracting the moving member information.

5. The ultrasound diagnosis apparatus according to claim 3, wherein the processing circuitry is further configured to separate a scan range formed with a plurality of scanning lines into plural sectional regions;
wherein the processing circuitry is further configured to extract a portion of the moving member information with respect to each of the plural sectional regions by using a respective statistical characteristic corresponding to the each of the plural sectional regions, and
wherein the processing circuitry is further configured to generate second image data based on the portions of the moving member information of the plural sectional regions.

6. The ultrasound diagnosis apparatus according to claim 5, wherein
each of the plural sectional regions overlaps with at least one other sectional region of the plural sectional regions, and
the processing circuitry is further configured to calculate a corresponding statistical characteristic of an overlapping region of at least two of the plural sectional regions.

7. The ultrasound diagnosis apparatus according to claim 5, wherein the processing circuitry is further configured to:
extract first moving member information by using the respective statistical characteristics calculated from the scan range formed with the plurality of scanning lines,
extract second moving member information of each of the plural sectional regions by using the respective statistical characteristic calculated from the each of the plural sectional regions, and
generate third image data based on the first moving member information and the second moving member information.

8. The ultrasound diagnosis apparatus according to claim 7, wherein
the processing circuitry is further configured to calculate a first power value as the first moving member information and a second power value as the second moving member information, and
the processing circuitry is further configured to generate the third image data based on the first moving member information and the second moving member information by multiplying at least one of the first and second power values by a coefficient, and further selecting a smaller value between (1) a result of multiplying at least one of the first and second power values, and (2) the first power value and the second power value not multiplied by the coefficient.

9. The ultrasound diagnosis apparatus according to claim 8, wherein the processing circuitry is further configured to generate the third image data, based on the first moving member information and the second moving member information, by (a) multiplying at least one of the first and second power values by the coefficient, (b) selecting the smaller value between (1) the result of multiplying at least one of the first and second power values, and (2) the first power value and the second power value not multiplied by the coefficient, and (c) generating the third image data based on the selected smaller value.

10. The ultrasound diagnosis apparatus according to claim 5, wherein
the processing circuitry is further configured to calculate an average value of the moving member information of each of the plural sectional regions, and correct the portions of the moving member information of the plural sectional regions by using the average values, and
the processing circuitry is further configured to generate the second image data based on the corrected portions of the moving member information of the plural sectional regions.

11. The ultrasound diagnosis apparatus according to claim 10, wherein the processing circuitry is further configured to correct the portions of moving member information of the plural sectional regions in such a manner that the average values are each equal to an average value of two or more adjacently-positioned sectional regions.

12. The ultrasound diagnosis apparatus according to claim 3, wherein
the processing circuitry is further configured to calculate a correlation matrix as the statistical characteristic, by using the saturation values for the plurality of frames,
the processing circuitry is further configured to calculate a filter coefficient used for suppressing a clutter component, based on a result of a principal component analysis performed by using the correlation matrix, and the processing circuitry is further configured to extract the moving member information by using the filter coefficient, based on the saturation values for the plurality of frames.

13. The ultrasound diagnosis apparatus according to claim 12, wherein the processing circuitry is further configured to calculate the filter coefficient by normalizing eigenvalues of correlation matrices of sectional regions obtained by separating an image while using a largest eigenvalue of a correlation matrix of an entirety of the image and further determining a rank cut number by using the normalized eigenvalues.

14. The ultrasound diagnosis apparatus according to claim 2, wherein, with respect to an observation point at which the analog reflected-wave signals are observed, the processing circuitry is further configured to interpolate the moving member information in a surrounding of the observation point into the moving member information of the observation point.

15. An ultrasound diagnosis apparatus, comprising: processing circuitry configured to
    extract a portion of moving member information with respect to each of plural sectional regions by using a statistical characteristic calculated from the plural sectional regions, the plural sectional regions being obtained by separating a scan range formed with a plurality of scanning lines into plural regions, the extraction being performed while using a data sequence represented by a set made up of portions of reflected-wave data generated through a phased addition process performed on reflected-wave signals generated by transmitting an ultrasound wave with respect to a mutually same scanning line;
    calculate an average value of the moving member information corresponding to each of the plural sectional regions and correct the portions of the moving member information of the sectional regions by using the average values in such a manner that the average value of the moving member information of the each of the plural sectional regions is each equal to an average value of at least two of the plural sectional regions that are adjacent to the each of the plural sectional regions; and
    generate image data based on the corrected portions of the moving member information of the plural sectional regions.

16. A medical image processing apparatus, comprising: processing circuitry configured to
    calculate, in accordance with an intensity of digital reflected-wave data generated through a phased addition process, a saturation value for analog reflected-wave signals observed before the phased addition process is performed, the analog reflected-wave signals being generated by transmitting an ultrasound wave with respect to a mutually same scanning line, and the digital reflected-wave data being digital signals generated by performing an analog to digital conversion on the analog reflected-wave signals;
    produce processed reflected-wave data by: (1) when the calculated saturation value is at least a threshold value indicating saturation, outputting as corresponding processed reflected-wave data, data obtained by multiplying the digital reflected-wave data by a predetermined coefficient having a non-zero value smaller than 1, and (2) when the calculated saturation value is less than the threshold value indicating saturation, outputting as the corresponding processed reflected-wave data, the digital reflected-wave data; and
    cause a display to display data based on the processed reflected-wave data.

17. A medical image processing apparatus, comprising: processing circuitry configured to
    extract a portion of moving member information with respect to each of plural sectional regions by using a statistical characteristic calculated from the plural sectional regions, the plural sectional regions being obtained by separating a scan range formed with a plurality of scanning lines into plural regions, the extraction being performed while using a data sequence represented by a set made up of portions of reflected-wave data generated through a phased addition process performed on reflected-wave signals generated by transmitting an ultrasound wave with respect to a mutually same scanning line;
    calculate an average value of the moving member information corresponding to each of the plural sectional regions, and correct the portions of the moving member information of the sectional regions by using the average values in such a manner that the average value of the moving member information of the each of the plural sectional regions is each equal to an average value of at least two of the plural sectional regions that are adjacent to the each of the plural sectional regions; and
    generate image data based on the corrected portions of the moving member information of the plural sectional regions.

18. A medical image processing method implemented by a computer, the method comprising:
    calculating, in accordance with an intensity of digital reflected-wave data generated through a phased addition process, a saturation value for analog reflected-wave signals observed before the phased addition process is performed, the analog reflected-wave signals being generated by transmitting an ultrasound wave with respect to a mutually same scanning line, and the digital reflected-wave data being digital signals generated by performing an analog to digital conversion on the analog reflected-wave signals;
    produce processed reflected-wave data by: (1) when the calculated saturation value is at least a threshold value indicating saturation, outputting as corresponding processed reflected-wave data, data obtained by multiplying the digital reflected-wave data by a predetermined coefficient having a non-zero value smaller than 1, and (2) when the calculated saturation value is less than the threshold value indicating saturation, outputting as corresponding processed reflected-wave data, the digital reflected-wave data; and
    causing a display to display data based on the processed reflected-wave data.

19. A medical image processing method implemented by a computer, the method comprising:
    extracting a portion of moving member information with respect to each of plural sectional regions by using a statistical characteristic calculated from the plural sectional regions, the plural sectional regions being obtained by separating a scan range formed with a plurality of scanning lines into plural regions, the extraction being performed while using a data sequence represented by a set made up of portions of reflected-wave data generated through a phased addition process performed on reflected-wave signals generated by transmitting an ultrasound wave with respect to a mutually same scanning line;

calculating an average value of the moving member information corresponding to each of the plural sectional regions and correcting the portions of the moving member information of the sectional regions by using the average values in such a manner that the average value of the moving member information of the each of the plural sectional regions is each equal to an average value of at least two of the plural sectional regions that are adjacent to the each of the plural sectional regions;

generating image data based on the corrected portions of the moving member information of the plural sectional regions; and causing a display to display the image data.

* * * * *